US012653662B2

(12) United States Patent
Brodie et al.

(10) Patent No.: US 12,653,662 B2
(45) Date of Patent: Jun. 16, 2026

(54) STENT GRAFT PROSTHESIS

(71) Applicant: Vascutek Limited, Renfrewshire (GB)

(72) Inventors: Robbie Brodie, Lanarkshire (GB);
Gary McDonald, Lanarkshire (GB);
Seonaid Nimmo, Lanarkshire (GB)

(73) Assignee: Vascutek Limited, Renfrewshire (GB)

( * ) Notice: Subject to any disclaimer, the term of this
patent is extended or adjusted under 35
U.S.C. 154(b) by 983 days.

(21) Appl. No.: 17/624,675

(22) PCT Filed: Jul. 6, 2020

(86) PCT No.: PCT/GB2020/051617
§ 371 (c)(1),
(2) Date: Jan. 4, 2022

(87) PCT Pub. No.: WO2021/005346
PCT Pub. Date: Jan. 14, 2021

(65) Prior Publication Data
US 2022/0273415 A1      Sep. 1, 2022

(30) Foreign Application Priority Data
Jul. 8, 2019    (GB) ...................................... 1909789

(51) Int. Cl.
*A61F 2/07*       (2013.01)
*A61F 2/89*       (2013.01)
(52) U.S. Cl.
CPC ................. *A61F 2/07* (2013.01); *A61F 2/89*
(2013.01); *A61F 2002/075* (2013.01); *A61F*
*2230/0095* (2013.01)
(58) Field of Classification Search
CPC ................ A61F 2/852; A61F 2002/075; A61F
2230/0095; A61F 2/07; A61F 2220/0008
See application file for complete search history.

(56) References Cited

U.S. PATENT DOCUMENTS

| | | | |
|---|---|---|---|
| 4,580,568 A | 4/1986 | Gianturco | |
| 5,290,305 A | 3/1994 | Inoue | |
| (Continued) | | | |

FOREIGN PATENT DOCUMENTS

| | | | |
|---|---|---|---|
| CA | 2872125 A1 | 4/2011 | |
| EP | 0855171 A2 | 7/1998 | |
| (Continued) | | | |

OTHER PUBLICATIONS

International Search Report and Written Opinion for International
Application No. PCT/GB2020/051617 dated Oct. 21, 2020.
(Continued)

*Primary Examiner* — Brian E Pellegrino
(74) *Attorney, Agent, or Firm* — Foley Hoag LLP;
Stephen J. Kenny; Nicole A. Bustos-Pomerantz

(57) ABSTRACT

A stent graft prosthesis for repair of a defective natural
vessel comprises a tubular fabric member having at least
first and second ends, wherein at least one of those ends is
supported by a combination of two cooperating ring stents of
different configurations, and the tubular fabric member is
attached at selected points to each ring stent, and at least one
ring stent is compressible into a folded saddle shape having
two peaks and two valleys, and the other ring stent crosses
over the saddle shape ring stent at four points, each point
being in a region between a peak and a valley of the folded
saddle shape. The other ring stent may be selected from ring
stents which when deployed, have a circular or cylindrical
shape, or a saddle shape, or one or more V-shaped hinge
portions with curvilinear portions therebetween, or a
Z-shaped stent.

14 Claims, 11 Drawing Sheets

(56) References Cited

U.S. PATENT DOCUMENTS

| | | |
|---|---|---|
| 5,578,072 A | 11/1996 | Barone et al. |
| 5,591,228 A | 1/1997 | Edoga |
| 5,683,451 A | 11/1997 | Lenker et al. |
| 5,824,041 A | 10/1998 | Lenker et al. |
| 5,925,074 A | 7/1999 | Gingras et al. |
| 6,036,723 A | 3/2000 | Anidjar et al. |
| 6,203,568 B1 | 3/2001 | Lombardi et al. |
| 6,635,080 B1 | 10/2003 | Lauterjung et al. |
| 6,673,103 B1 | 1/2004 | Golds et al. |
| 6,773,457 B2 | 8/2004 | Ivancev et al. |
| 6,938,646 B2 | 9/2005 | Litton |
| 7,780,622 B2 | 8/2010 | Fitzpatrick et al. |
| 7,901,446 B2 | 3/2011 | Fitzpatrick et al. |
| 8,088,155 B1 | 1/2012 | Lauterjung |
| 8,088,159 B2 | 1/2012 | Lauterjung |
| 8,092,511 B2 | 1/2012 | Chuter |
| 8,486,129 B2 | 7/2013 | Lautherjung |
| 8,652,195 B2 | 2/2014 | Tani |
| 8,652,198 B2 | 2/2014 | Andreas et al. |
| 8,740,971 B2 | 6/2014 | Iannelli |
| 8,968,389 B2 | 3/2015 | Greenberg et al. |
| 9,056,002 B2 | 6/2015 | Tabor |
| 9,398,964 B2 | 7/2016 | McGee et al. |
| 9,510,936 B2 | 12/2016 | McDonald et al. |
| 9,622,894 B2 | 4/2017 | McGee |
| 9,788,983 B2 | 10/2017 | Johnson et al. |
| 9,993,329 B2 | 6/2018 | McDonald et al. |
| 10,137,021 B2 | 11/2018 | McDonald et al. |
| 10,219,890 B2 | 3/2019 | Madjarov et al. |
| 10,413,396 B2 | 9/2019 | Ashton |
| 10,724,805 B2 | 7/2020 | Barmeier et al. |
| 11,026,823 B2 | 6/2021 | McDonald et al. |
| 11,458,008 B2 | 10/2022 | Debus et al. |
| 11,471,261 B2 | 10/2022 | McDonald |
| 11,554,033 B2 | 1/2023 | Kolbel et al. |
| 12,023,236 B2 | 7/2024 | Debus et al. |
| 12,048,621 B2 | 7/2024 | Nelis |
| 12,115,059 B2 | 10/2024 | Mcdonald et al. |
| 12,127,961 B2 | 10/2024 | McDonald et al. |
| 2003/0024527 A1 | 2/2003 | Ginn |
| 2003/0120263 A1 | 6/2003 | Ouriel et al. |
| 2003/0130720 A1 | 7/2003 | DePalma et al. |
| 2003/0135257 A1 | 7/2003 | Taheri |
| 2003/0176911 A1 | 9/2003 | Iancea et al. |
| 2004/0117003 A1 | 6/2004 | Ouriel et al. |
| 2004/0167618 A1 | 8/2004 | Shaolian et al. |
| 2004/0215315 A1 | 10/2004 | Jones et al. |
| 2004/0243221 A1 | 12/2004 | Fawzi et al. |
| 2005/0033399 A1 | 2/2005 | Richter |
| 2005/0060029 A1 | 3/2005 | Le et al. |
| 2005/0075725 A1 | 4/2005 | Rowe |
| 2005/0137681 A1 | 6/2005 | Shoemaker et al. |
| 2005/0230956 A1 | 10/2005 | Igeta |
| 2006/0184226 A1 | 8/2006 | Austin |
| 2006/0229700 A1 | 10/2006 | Acosta et al. |
| 2007/0010873 A1 | 1/2007 | Neri |
| 2007/0055347 A1 | 3/2007 | Arbefeuille |
| 2007/0106368 A1 | 5/2007 | Vonderwalde |
| 2007/0112422 A1 | 5/2007 | Dehdashtian |
| 2007/0135904 A1 | 6/2007 | Eidenschink et al. |
| 2007/0168013 A1 | 7/2007 | Douglas |
| 2007/0208409 A1 | 9/2007 | Quigley |
| 2008/0082159 A1 | 4/2008 | Tseng et al. |
| 2008/0147171 A1 | 6/2008 | Ashton et al. |
| 2008/0188924 A1 | 8/2008 | Prabhu |
| 2009/0043330 A1 | 2/2009 | To |
| 2009/0264991 A1 | 10/2009 | Paul, Jr. et al. |
| 2010/0152835 A1 | 6/2010 | Orr |
| 2010/0222869 A1 | 9/2010 | Delaney |
| 2010/0234937 A1 | 9/2010 | Wang et al. |
| 2011/0054586 A1 | 3/2011 | Mayberry et al. |
| 2011/0066221 A1 | 3/2011 | White et al. |
| 2011/0190862 A1 | 8/2011 | Bashiri et al. |
| 2011/0230956 A1 | 9/2011 | White |
| 2012/0059448 A1 | 3/2012 | Parker et al. |
| 2012/0136431 A1 | 5/2012 | Chen |
| 2012/0158121 A1 | 6/2012 | Ivancev et al. |
| 2012/0172887 A1 | 7/2012 | Hatfield |
| 2012/0239136 A1 | 9/2012 | Bruzzi |
| 2012/0271401 A1 | 10/2012 | Bruszewski et al. |
| 2012/0277849 A1 | 11/2012 | Tani et al. |
| 2012/0290068 A1 | 11/2012 | Roeder et al. |
| 2013/0131775 A1 | 5/2013 | Hadley et al. |
| 2013/0166015 A1 | 6/2013 | Roeder |
| 2013/0218138 A1 | 8/2013 | Fargahi |
| 2013/0289700 A1 | 10/2013 | Acosta-Acevedo |
| 2013/0289713 A1 | 10/2013 | Pearson et al. |
| 2014/0005586 A1 | 1/2014 | Feinstein |
| 2014/0194970 A1 | 7/2014 | Chobotov |
| 2014/0200648 A1 | 7/2014 | Newell et al. |
| 2014/0249617 A1 | 9/2014 | Argentine et al. |
| 2014/0257452 A1 | 9/2014 | Slazas et al. |
| 2014/0277332 A1 | 9/2014 | Slazas et al. |
| 2014/0277345 A1 | 9/2014 | Havel et al. |
| 2014/0277359 A1 | 9/2014 | Slazas et al. |
| 2015/0081004 A1 | 3/2015 | Takahashi et al. |
| 2015/0105819 A1 | 4/2015 | Becking et al. |
| 2015/0190221 A1 | 7/2015 | Schaefer et al. |
| 2015/0257910 A1 | 9/2015 | Duong et al. |
| 2015/0265444 A1 | 9/2015 | Kitaoka |
| 2016/0175132 A1 | 6/2016 | Wilger et al. |
| 2016/0235517 A1 | 8/2016 | Sethna et al. |
| 2017/0014221 A1 | 1/2017 | Kelly |
| 2018/0228593 A1 | 8/2018 | Eaton et al. |
| 2019/0192273 A1 | 6/2019 | Debus et al. |
| 2019/0223996 A1 | 7/2019 | McDonald |
| 2020/0038169 A1 | 2/2020 | Nelis |
| 2020/0038184 A1 | 2/2020 | McLean |
| 2020/0038211 A1 | 2/2020 | Kolbel et al. |
| 2020/0214821 A1 | 7/2020 | Mcdonald |
| 2021/0204954 A1 | 7/2021 | Nimmo |
| 2021/0212846 A1 | 7/2021 | Shahriari |
| 2021/0228330 A1 | 7/2021 | Kelly |
| 2021/0236257 A1 | 8/2021 | Walzman |
| 2021/0299424 A1 | 9/2021 | King |
| 2021/0307641 A1 | 10/2021 | Rumbles et al. |
| 2022/0023080 A1 | 1/2022 | Mcdonald |
| 2022/0023081 A1 | 1/2022 | Mcdonald |
| 2022/0273415 A1 | 9/2022 | Brodie et al. |
| 2022/0378569 A1 | 12/2022 | Mcdonald |
| 2023/0015592 A1 | 1/2023 | Debus et al. |
| 2023/0119898 A1 | 4/2023 | Kölbel et al. |
| 2023/0225853 A1 | 7/2023 | Zeitani et al. |
| 2024/0293219 A1 | 9/2024 | Debus et al. |
| 2025/0041090 A1 | 2/2025 | McDonald et al. |

FOREIGN PATENT DOCUMENTS

| | | | |
|---|---|---|---|
| EP | 0880979 | A1 | 12/1998 |
| EP | 1736116 | A2 | 12/2006 |
| EP | 1847236 | A2 | 10/2007 |
| EP | 2606852 | A1 | 6/2013 |
| EP | 2676639 | A1 | 12/2013 |
| EP | 3115022 | A1 | 1/2017 |
| EP | 3248572 | A1 | 11/2017 |
| EP | 3323385 | A1 | 5/2018 |
| GB | 2470083 | A | 11/2010 |
| GB | 2491477 | A | 12/2012 |
| GB | 2517689 | A | 3/2015 |
| JP | H07308330 | A | 11/1995 |
| JP | 2017042236 | A | 3/2017 |
| RU | 2720745 | C1 | 5/2020 |
| WO | WO-01/024735 | A1 | 4/2001 |
| WO | WO-2004/017866 | A1 | 3/2004 |
| WO | WO-2004/064686 | A1 | 8/2004 |
| WO | WO-2006/019626 | A2 | 2/2006 |
| WO | WO-2006/034340 | A1 | 3/2006 |
| WO | WO-2006/088638 | A1 | 8/2006 |
| WO | WO-2008/057569 | A1 | 5/2008 |
| WO | WO-2008/088835 | A1 | 7/2008 |
| WO | WO-2008/112270 | A1 | 9/2008 |
| WO | WO-2009/009376 | A2 | 1/2009 |
| WO | WO-2009/082718 | A1 | 7/2009 |
| WO | WO-2009/153768 | A1 | 12/2009 |

(56) References Cited

FOREIGN PATENT DOCUMENTS

| | | | |
|---|---|---|---|
| WO | WO-2010/053563 | A1 | 5/2010 |
| WO | WO-2012/043011 | A1 | 4/2012 |
| WO | WO-2013/152327 | A1 | 10/2013 |
| WO | WO-2014/096811 | A2 | 6/2014 |
| WO | WO-2014/163957 | A1 | 10/2014 |
| WO | WO-2015/138778 | A1 | 9/2015 |
| WO | WO-2016/054537 | A1 | 4/2016 |
| WO | WO-2016075615 | A3 | 6/2016 |
| WO | WO-2016/112378 | A1 | 7/2016 |
| WO | WO-2017/136733 | A1 | 8/2017 |
| WO | WO-2017/203056 | A1 | 11/2017 |
| WO | WO-2018/156848 | A1 | 8/2018 |

OTHER PUBLICATIONS

International Search Report and Written Opinion of the International Searching Authority for International Application No. PCT/GB2017/052602 mailed on Jan. 9, 2018.

European Search Report issued in European Patent Application No. 17767890.1, Jul. 28, 2020, 7 pages.

International Preliminary Report on Patentability for Application No. PCT/GB2021/052337 dated Mar. 23, 2023.

Levack et al., "Rapid Aortic Arch Debranching Using the Gore Hybrid Vascular Graft," Ann Thorac Surg, 95: e163-e165 (2013).

Nigro et al., "Use of the Gore Hybrid Vascular Graft in a challenging high-lying extracranial carotid artery aneurysm," J Vasc Surg, 59: 817-820 (2014).

Parodi, J.C., et al., "Transfemoral Intraluminal Graft Implantation for Abdominal Aortic Aneurysms," Annals of Vascular Surgery, vol. 5, pp. 491-499 (1991).

Shrestha et al., "Total aortic arch replacement with a novel 4-branched frozen elephant trunk prosthesis: Single-center results of the first 100 patients," Journal of Thoracic and Cardiovascular Surgery, 152(1): 148-159 (2016).

300

300

STENT GRAFT PROSTHESIS

RELATED APPLICATIONS

This application is a national-stage application under 35 USC § 371 based on PCT/GB2020/051617, filed Jul. 6, 2020; which claims the benefit of priority to Great Britain (UK) Patent Application 1909789.8, filed on Jul. 8, 2019.

This disclosure relates to prosthetic devices deployable at a target treatment site within a lumen of a natural vessel for the purposes of compensating for decline in the ability of the natural vessel to perform its natural function due to disease, injury or a natural aging process of a patient. In particular, improvements in the manner of securing the prosthetic device at a target treatment site are disclosed.

BACKGROUND

Artificial prostheses consisting of a tubular conduit having an open lumen are well-known and have been used in surgical and hybrid surgical procedures. Currently there is a preference for using minimally-invasive delivery systems in suitable cases to place a prosthesis at an internal treatment site to replace a diseased or damaged natural body lumen, such as, for example, a blood vessel or any of the other hollow organs for example bile ducts, sections of intestine or the like. The most common use of such artificial prostheses is to replace diseased or damaged blood vessels.

A number of vascular disorders, can be treated by use of an artificial prosthesis. One such disorder is dissection where an inner layer of a natural vessel such as the aorta tears or separates, for example in aortic dissection the intima may tear away from the media admitting rapid blood influx through the tear leading to progressive separation, unnatural vessel expansion, and/or blood leakage (haemorrhage). Blood may flow in between the layers of the blood vessel to such an extent that the aorta may rupture, or the diverted blood flow may result in insufficient blood flow (ischaemia) to organs.

Another relatively common vascular disorder is an aneurysm. Aneurysm occurs when a section of natural blood vessel wall, typically of the aortic artery, dilates and balloons outwardly. Whilst small aneurysms cause little or no symptoms, larger aneurysms pose significant danger to a patient. Rupture of an aortic aneurysm can occur without warning and is usually fatal, so significant emphasis is placed on early diagnosis and treatment. With an increasing ageing population, the incidence of aneurysm continues to rise in western societies.

Provided that an aneurysm is diagnosed prior to rupture, surgical treatment to repair the affected vessel wall is effective. Surgical treatment of aneurysm involves the replacement or reinforcement of the aneurismal section of aorta with a synthetic graft or prostheses under general anaesthesia allowing the patient's abdomen or thorax to be opened (see Parodi et al., Annals of Vascular Surgery (1991) 5:491-499). The patient will then have a normal life expectancy.

Currently, aneurysm or dissection repair often involves the delivery by catheter of a fabric or ePTFE graft which is retained at the required location by deployment of metallic stent elements. The ability to deliver the graft/stent device by catheter reduces the surgical intervention to a small cut-down to expose the femoral artery and, in suitable circumstances, the device can be deployed percutaneously. Catheter delivery is beneficial since the reduced invasive nature of the procedure allows utilisation of a local anaesthetic and leads to reduced mortality and morbidity, as well as decreased recovery time. For example, endovascular repair is typically used for repair of infra-renal abdominal aortic aneurysms where the graft is placed below the renal arteries. Many different types of devices useful for endovascular repair are now available, for example a resiliently engaging endovascular element described in U.S. Pat. No. 6,635,080 (Vascutek) or a tubular fabric liner having a radially expandable supporting frame and a radiopaque marker element stitched to the liner as disclosed in U.S. Pat. No. 6,203,568 (Medtronic).

Endovascular techniques involve the delivery of a prosthesis by catheter. Since the internal lumen of the catheter defines the maximum dimensions of the prostheses to be inserted, much effort has been expended in the design of prostheses which can be packaged in a minimal volume, and are easy to deploy once positioned at the required location.

One successful type of prosthesis, is a "stent graft" comprising a conduit formed from a flexible sleeve attached to a rigid support or stent. The sleeve will typically be made of a physiologically acceptable fabric (usually a knitted or woven fabric) of expanded polytetrafluoroethylene (ePTFE), PTFE or polyester, polyethylene, or polypropylene and may optionally be coated to reduce friction; discourage clotting or to deliver a pharmaceutical agent. Coatings for the fabric or its constituent fibres include heparin, gelatin, collagen, or an antibacterial such as rifampicin. The fabric may be porous on at least one surface to enable cell in-growth. These materials are suitable for the presently disclosed stent graft prosthesis. The stent may be balloon-expandable (e.g. a PALMAZ stent made of rigid stainless steel wire), but could also be self-expandable and formed of a shape memory material, such as nitinol (a nickel-titanium alloy). Numerous different stent designs are known in the art, for example braided stents as described in EP 880979 or wire "zig-zag" stents as described in U.S. Pat. No. 4,580, 568. Typically the stent designs accommodate the requirement for compact packaging for delivery by radial or axial deformation or combinations thereof to a slim configuration temporarily held by means of a removable sleeve or release wires.

Another useful design is a saddle"-shape ring stent which can be formed from wire into an individual circular ring stent that is normally planar (undistorted from the natural ring), but which is sufficiently resilient to be distorted (folded) so that a first pair of diametrically opposed points on the circumference of the ring stent are displaced in one axial direction whilst a second pair of diametrically opposed points, centrally located on the circumference between the first pair, are displaced in the opposing axial direction to form a symmetrical "saddle"-shaped configuration. For convenience, the first pair of points can be described as "peaks", with the second pair of points being described as "valleys" or vice versa. The peaks and valleys are typically fastened to a tubular sleeve component of a graft prosthesis. The degree of axial displacement between the first pair of points and the second pair of points (which axial displacement is also termed the "saddle height"), is a function of the original circumference of the ring stent prior to its distortion (folding), relative to the final circumference of a circle within which the distorted (folded saddle shape) configuration can be located. Thus, the ratio of final circumference:original circumference provides a simplistic notation of the axial displacement. Generally the final circumference will be the outer circumference of the graft sleeve to which the stent is to be attached. The percentage oversize of the undistorted inner circumference of the circular stent relative to the outer circumference of the graft sleeve also gives a convenient measure of the "saddle" shape adopted, and can be calculated as:

$$Oversize \% = \frac{[Stent\ inner\ diameter - Graft\ sleeve\ outer\ diameter]}{Graft\ sleeve\ outer\ diameter} \times 100\%$$

SUMMARY

A stent graft prosthesis for repair of a defective natural vessel comprises a tubular fabric member having at least first and second ends, wherein at least one of those ends is supported by a combination of two cooperating ring stents of different configurations, and the tubular fabric member is attached at selected points to each ring stent, and at least one ring stent is compressible into a folded "saddle" shape having two peaks and two valleys, and the other ring stent crosses over the "saddle" shape ring stent at four points, each point being in a region between a peak and a valley of the folded "saddle" shape. The other ring stent may be selected from ring stents which when deployed, have a circular or cylindrical shape, or a saddle shape, or one or more V-shaped hinge portions with curvilinear portions therebetween, or a "Z"-shaped stent.

In particular a disclosed stent graft prosthesis comprises:

a tubular fabric member having at least first and second ends, and a length $L_f$ extending between the first and second ends, and having an open lumen diameter $D_f$;

wherein at least one of the first and second ends of the tubular fabric member is supported by a combination of two cooperating ring stents of different configurations, and each one of the two cooperating ring stents of different configurations is compressible into a folded shape to provide a compact delivery form of the stent graft prosthesis, and the tubular fabric member is attached at selected points to each of the two cooperating ring stents of different configurations, and at least one of the two cooperating ring stents of different configurations is compressible into a folded "saddle" shape having two peaks and two valleys, and the other one of the two cooperating ring stents of different configurations crosses over the at least one of the two cooperating ring stents of different configurations at four points, each point being in a region between a peak and a valley of the folded "saddle" shape.

A stent graft prosthesis may be configured such that the other one of the two cooperating ring stents of different configurations is also compressible into a folded "saddle" shape having two peaks and two valleys, and a peak thereof is axially aligned with a peak of the at least one of the two cooperating ring stents of different configurations.

A stent graft prosthesis may be configured such that the other one of the two cooperating ring stents of different configurations that is compressible into a folded shape is a shape-set ring stent having at least one "V"-shaped hinge portion, and that "V"-shaped hinge portion is axially aligned with a peak of the at least one of the two cooperating ring stents of different configurations.

A stent graft prosthesis is disclosed herein which comprises:

a tubular fabric member having at least first and second ends, and a length $L_f$ extending between the first and second ends. The length $L_f$ being the longest dimension of continuous tubular fabric member aligned with the longitudinal axis of the tubular fabric member. The tubular fabric member has an open lumen diameter $D_f$. At least one of the first and second ends of the tubular fabric member is supported by a combination of two cooperating ring stents of different configurations. Each one of the two cooperating ring stents of different configurations is compressible into a folded shape for the purpose of compactly packaging the stent graft prosthesis for delivery into a lumen of a vessel. The tubular fabric member optionally may be supported throughout its length by one or more additional stents which may be the same as, or different from either one of the two cooperating ring stents of different configurations. Notably, none of any additional stents, or combinations thereof, which may be independently placed at an intermediate position or at spaced intervals between the first and second ends contact either one of the two cooperating ring stents of different configurations in the combination of two cooperating ring stents of different configurations when the stent graft prosthesis is fully deployed and the lumen of the tubular fabric member is open. Alternatively stated, in the intended use within a natural vessel, the combination of two cooperating ring stents of different configurations located at the first or second ends, or at each end, of the tubular fabric member do not engage with any other additional stent used to support the tubular graft member within its length, and function independently from any such other additional stent (if present). The combination of two cooperating ring stents of different configurations located at either or each end of the tubular fabric member function, when the stent graft prosthesis is deployed in an operational configuration within a lumen of a vessel, to maintain a desired open round configuration, acting to counter any tendency of the open end to distort, oval, or flatten as may be observed for example in use of a single steep saddle-shaped ring stent. The term "steep" is applicable to a ring stent which when folded into a saddle shape for example has "peaks" and "valleys" having a significant axial distance between the extent of a peak extending in one axial direction and the extent of a valley extending in the opposite axial direction.

The term "a combination of two cooperating ring stents of different configurations," relates to a functional association of two individual ring stents, each one of the two ring stents differing from the other in terms of certain aspects of its physical configuration, its folded and deployed forms, and optionally the attachment thereof to a portion of the tubular graft member, such that the two ring stents interact to provide improvements in the location and radial stability of the stent graft prosthesis whilst not being joined together. Thus parts of the respective ring stents may overlap or slide across intersecting parts, one within the other during folding and deployment of the stent graft prosthesis. The interacting relationship of the combination of two cooperating ring stents of different configurations may be facilitated by selectively attaching the respective cooperating ring stents to end portions of the tubular graft member of the stent graft prosthesis.

The combination of two cooperating ring stents of different configurations may comprise ring stents selected from foldable ring stents which when deployed have a circular or cylindrical shape, foldable ring stents which when deployed have a saddle shape, and foldable ring stents having one or more V-shaped hinge portions and curvilinear portions therebetween, provided that in the said combination of two cooperating ring stents of different configurations only one foldable ring stent may be of circular or cylindrical shape. Where a foldable ring stent having multiple "V" shaped hinge portions connected together as one of the two cooperating ring stents of different configurations, that type of ring stent may be referred to as a "Z"-shaped stent. The foldable ring stents which when deployed have a saddle shape may be individually selected from those whose deployment shape is one selected from a range including those forming steep saddle shapes to those forming less steep saddle shapes. As used herein the term "steep" is useful in comparing ring stents used in the combination of two cooperating ring stents of different configurations, where one ring stent when folded can be considered relative to the other ring stent when folded and confined for delivery for example, or for differentiating the ring stents, one relative to the other, in the combination of two cooperating ring stents of different configurations when in the deployed state.

The combination of two cooperating ring stents of different configurations comprises ring stents where one of the two cooperating ring stents of different configurations crosses the other one of the two cooperating ring stents of different configurations.

Thus one of the two cooperating ring stents of different configurations can be considered to be inside the other, or one is an external ring stent and the other is an internal ring stent. Generally the external ring performs a sealing functionality to hold the fabric of the tubular fabric member against for example a surface of a healthy portion of natural vessel so that the end of the stent graft prosthesis is adequately sealed in its desired location. Furthermore, in general the internal ring serves to ensure shape retention, especially radial stability, for the end of the tubular fabric member of the stent graft prosthesis, for example to resist over-dilation of the open lumen, such as flattening, ovalling, petalling, stretching, or inhibit any tendency of the lumen at the deployed end of the stent graft prosthesis to distort from the design configuration in one lumen cross-dimension or another.

The following illustrative, but non-exhaustive list of embodiments of combinations of two cooperating ring stents of different configurations which may be useful for locating and stabilising at least one end of the stent graft prosthesis:

an internal steep saddle shaped ring stent with an external less steep saddle shaped ring stent;

an internal steep saddle shaped ring stent with an external circular or cylindrical ring stent;

an external steep saddle shaped ring stent with an internal less steep saddle shaped ring stent;

an external steep saddle shaped ring stent with an internal circular or cylindrical ring stent;

an internal shape-set ring stent having at least one "V"-shaped flexible hinge portion with curvilinear portions on either side of the at least one shape set "V"-shaped portion, or between the more than one "V"-shaped flexible hinge portions, and an external less steep saddle shaped ring stent;

an internal shape-set ring stent having at least one "V"-shaped flexible hinge portion with curvilinear portions on either side of the at least one shape set "V"-shaped portion, or between the more than one "V"-shaped flexible hinge portions, and an external circular or cylindrical ring stent;

an internal radially compressible Z-stent with an external steep saddle shaped ring stent; and an internal radially compressible Z-stent with an external circular or less steep saddle shaped ring stent.

There is disclosed herein a stent graft prosthesis comprising:

a tubular fabric member having at least first and second ends, and a length $L_f$ extending between the first and second ends, and having an open lumen diameter $D_f$;

wherein at least one of the first and second ends of the tubular fabric member is supported by a combination of two cooperating ring stents of different configurations, and each one of the two cooperating ring stents of different configurations is compressible into a folded shape for delivery of the stent graft prosthesis to a treatment site, and the tubular fabric member is attached at selected points to each of the two cooperating ring stents of different configurations, and the two cooperating ring stents of different configurations are free to move relative to one another at points where one of the two cooperating ring stents of different configurations crosses the other one of the two cooperating ring stents of different configurations, and the different configurations of the two cooperating ring stents includes that one of the two cooperating ring stents of different configurations is constrained from over-dilation by the other one of the two cooperating ring stents of different configurations.

The different configurations of the two cooperating ring stents may include that one of the two cooperating ring stents of different configurations is a relatively steep "saddle"-shape ring which is constrained from over-dilation by the other one of the two cooperating ring stents of different configurations.

The different configurations of the two cooperating ring stents may include that one of the two cooperating ring stents of different configurations is a relatively steep shape-set ring which constrains a shallower (non-shape set) ring stent from over-dilation, the latter being the other one of the two cooperating ring stents of different configurations.

In embodiments, in the combination of two cooperating ring stents of different configurations one of the two cooperating ring stents of different configurations may comprise a ring stent which, when the stent graft prosthesis is fully deployed and the lumen of the tubular fabric member is open, is substantially circular or less steep than the other one of the two cooperating ring stents of different configurations, and is located external to the other one of the two cooperating ring stents of different configurations. The other one of the two cooperating ring stents may be of a relatively steep saddle shape. In such embodiments the circular or less steep ring stent acts as the main sealing ring for an end of the stent graft prosthesis when deployed.

In embodiments, one or more ring stents may be deployed with the assistance of an expandable balloon.

A ring stent in the combination of two cooperating ring stents of differing configurations may be formed from a shape-memory material, and capable of being compactly folded and returning to a desired shape for that use, and to facilitate folding into a compact package for delivery, for example within a restraining delivery sheath. When deployed, for example by removal of a restraining delivery sheath, each ring stent in the combination of two cooperating ring stents of differing configurations opens and tends towards adopting the desired configuration within the constraint of the attached tubular fabric member and any additional constraint imposed by the natural vessel into which the stent graft prosthesis has been deployed.

A desired configuration for a compressible ring stent in a deployed stent graft prosthesis can be ensured after a restraining delivery sheath is removed by previous attachment of the ring stent to the tubular fabric member at selected discrete points, for example by means of sutures before the stent graft prosthesis is packaged in the restraining delivery sheath.

At least one ring stent in the combination of two cooperating ring stents of differing configurations may be radially expandable from a compact configuration to a circular or part-cylindrical configuration. The at least one ring stent in the combination of two cooperating ring stents of differing configurations which may be radially expandable may have one or more V-shaped hinge portions and curvilinear portions therebetween. Alternatively at least one ring stent in the combination of two cooperating ring stents of differing configurations which may be radially expandable may have multiple "V" shaped hinge portions connected together to provide a "Z"-shaped stent.

At least one ring stent in the combination of two cooperating ring stent may be a "saddle shaped" ring stent, portions of which move both axially and radially when being folded into a compact configuration or when being deployed into an expanded configuration.

The radially expandable ring stent in the combination of two cooperating ring stents of differing configurations may be located within the "saddle shaped" ring stent, and attached at selected points to the tubular fabric member. This configuration urges the "saddle-shaped" ring stent to maintain a generally circular form in axial cross-section within the tubular fabric member, and inhibits a deformation observed with unsupported "saddle-shaped" ring stents and referred to in the field as "petalling", or "ovalling" due to the flattening of the open end of the tubular fabric member from the desired open circular configuration.

In embodiments of the stent graft prosthesis, a shape-set ring stent having at least one "V"-shaped hinge portion is positioned at least in part within the other one of the two cooperating ring stents of different configurations, which other one of the two cooperating ring stents of different configurations is compressible into a "saddle"-shape having peak and valley portions, and the shape-set ring stent is attached to the fabric of the tubular fabric member by the "V"-shaped hinge portion, or respective "V"-shaped hinge portions of the shape-set ring stent, at a peak of the "saddle"-shaped ring stent.

In embodiments of the stent graft prosthesis the tubular fabric member has a substantially circular perimeter at each of the first and second ends, and the ring stent which is compressible into a "saddle"-shape is attached to the fabric of the tubular fabric member at multiple points around the perimeter of one of the first and second ends, and the cooperating shape-set ring stent is selectively attached to parts of the fabric of the tubular fabric member at the same end to allow the ring stent which is compressible into a "saddle"-shape having peak and valley portions to slide when necessary on the shape-set ring stent, for example during folding to compact the stent graft prosthesis for delivery into a lumen of a natural vessel, or when deploying the stent graft prosthesis in a lumen of a natural vessel.

The combination of two cooperating ring stents of different configurations is found to provide effective end-sealing and radial stability for migration resistance functionality for the tubular graft prosthesis which is important for long term implantation.

Use of a shape-set foldable ring stent having one or more V-shaped hinge portions and curvilinear portions therebetween in combination with an outer ring stent that is compressible into a folded "saddle" shape having two peaks and two valleys portions, provides combined end-sealing stents for a tubular fabric member of a stent graft prosthesis to be deployed as a repair in a natural vessel. The "saddle" shaped end ring stent having two peak and two valley portions is configured as the overlying outer ring stent and slidably crossing portions of the shape-set foldable ring stent whereby upon deployment of the stent graft prosthesis the shape-set ring stent expands radially, and perpendicularly to the walls of the natural vessel being repaired which radial expansion urges the "saddle" shaped ring stent into a desired round cross-sectional shape whilst preventing the outer "saddle" shaped end ring stent from distorting into a so-called "petal"-shape or "ovalling" deformation.

Alternatively each ring stent in the combination of two cooperating ring stents of differing configurations may be of a "saddle-shape" type and having a differing saddle height from each other.

According to an embodiment of the stent graft prosthesis, the first and second ends of the tubular fabric member are each supported by a ring stent combinations, each such ring stent combination consisting of two cooperating ring stents of different configurations. Optionally, the continuous tubular fabric member extending between the first and second ends is supported by spaced apart ring stents, which need not be the same as the ring stent combination supporting each end of the tubular fabric member.

The first and second ends of the tubular fabric member may be referred to herein as the "proximal" and "distal" ends meaning respectively an end of the stent graft prosthesis that is nearer the heart when deployed, and farther from the heart when deployed.

In an embodiment of the stent graft prosthesis, the stent graft prosthesis may employ respectively in each ring stent combination either an outer "saddle"-shaped ring stent, or plain circular ring stent, which overlaps and constrains an inner steeper "saddle"-shaped ring stent to address the potential problem of long term vessel over-dilation due to the radially expansive force of self-expanding ring stents. The overlapping ring stent combination also results in good apposition of the deployed ring stents with respect to the vessel walls for sealing purposes due to the inner ring stent applying a radially directed force to hold the outer ring stent and fabric of the tubular fabric member securely against the vessel wall.

In embodiments of the stent graft prosthesis, each of the two cooperating ring stents of different configurations that is compressible into a folded shape is compressible into a "saddle"-shape having peak and valley portions, wherein one of the two cooperating ring stents has an uncompressed diameter $d_1$ that is equal to or greater than the open lumen diameter $D_f$ of the tubular fabric member and the other one of the two cooperating ring stents has an uncompressed diameter $d_2$ that is greater than the open lumen diameter $D_f$ of the tubular fabric member and that is significantly greater than the diameter $d_1$, and the one of the two cooperating ring stents which has an uncompressed diameter $d_1$ overlaps the other one of the two cooperating ring stents which has an uncompressed diameter $d_2$ so as to constrain the latter without being attached to it. In such embodiments, the one of the two cooperating ring stents which has an uncompressed diameter $d_1$ typically crosses over the other one of the two cooperating ring stents which has an uncompressed diameter $d_2$ at 4 points of intersection, each point of intersection lying in a region between peak and valley portions of the ring stent which has an uncompressed diameter $d_2$.

In such embodiments, the one of the two cooperating ring stents which has an uncompressed diameter $d_1$ may be identified as a "less steep saddle"-shape ring stent (LS) and the other one of the two cooperating ring stents which has an uncompressed diameter $d_2$ may be identified as a "steep saddle"-shape ring stent (S).

In embodiments the stent graft prosthesis may be branched, for example bifurcated.

It will be understood by those in the art that the tubular fabric member serves as a repair sleeve or liner to extend through and span a weakened or defective portion of a natural vessel, and that stents positioned at the first and second ends serve to locate the tubular fabric member so that it remains resident after a treatment procedure is completed upon the weakened or defective portion of the natural vessel, and delivery system components are removed. Those stents positioned at the first and second ends which serve to locate the tubular fabric member so that it remains resident after a treatment procedure is completed need not be of the same design or configuration as long as at least one end has two cooperating ring stents of different configurations as claimed.

In embodiments, each one of the two cooperating ring stents of different configurations has at least one portion attached to the fabric of the tubular fabric member, and each one of the two cooperating ring stents of different configurations has at least one portion in sliding contact with a portion of the other one of the two cooperating ring stents of different configurations. Thereby each one of the two cooperating ring stents of different configurations can be folded and deployed according to its characteristics, but by overlapping portions of the two cooperating ring stents of different configurations improvements in the profile and shape of the ends of the tubular fabric body are obtained such that the performance of the stent graft prosthesis is enhanced.

It will be appreciated that the ring stents initially, i.e. before folding, have a widest transverse dimension, conveniently referred to herein as a diameter, and may be in some cases entirely undeformed circular rings, or mainly circular rings with at least one, preferably two, shape-set parts such as flexible hinge portions or sinusoidal portions (as disclosed hereinbelow). Upon folding to provide a compactly folded stent for delivery purposes within a delivery restraint such as a sheath that "diameter" reduces to allow passage of the stent within a narrow lumen of a tubular vessel. In such a compactly folded state, at least a sinusoidal portion of at least one of the ring stents may be displaced axially along the longitudinal axis of the tubular fabric member. Thus the "diameter" of the ring stent has to be considered in the context as to whether it is in its original unfolded state, attached to a tubular fabric member so as to have a folded shape, in a compacted form for delivery within a restraint such as a removable sheath, or in a deployed configuration supporting the open end of the tubular graft prosthesis within a lumen of a vessel.

Shape-setting of "shape-memory" materials is generally known, and usually involves manipulation of the material around a shape-former which for a wire-formed ring in the instant invention may be a cylindrical or polygonal mandrel, under a heat treatment process which may involve controlled successive application of heat and quench stages. US 2009/0309273 for example discloses a method of making a self-expanding tubular stent from a shape-memory alloy.

In embodiments, in the combination of two cooperating ring stents of different configurations, at least one of the two cooperating ring stents of different configurations that is compressible into a folded shape has an uncompressed diameter that exceeds the open lumen diameter $D_f$ of the tubular fabric member.

In embodiments, in the combination of two cooperating ring stents of different configurations, each one of the two cooperating ring stents of different configurations that is compressible into a folded shape has an uncompressed diameter that equals or exceeds the open lumen diameter $D_f$ of the tubular fabric member.

In embodiments, in the combination of two cooperating ring stents of different configurations, one of the two cooperating ring stents of different configurations that is compressible into a folded shape has a diameter that exceeds the diameter of the other one of the two cooperating ring stents of different configurations that is compressible into a folded shape.

Each of the two cooperating ring stents of different configurations that is compressible into a folded shape is compressible into a "saddle"-shape having peak and valley portions, wherein one of the two cooperating ring stents (LS) has an uncompressed diameter $d_1$ that is equal to or greater than the open lumen diameter $D_f$ of the tubular fabric member and the other one of the two cooperating ring stents (S) has an uncompressed diameter $d_2$ that is greater than the open lumen diameter $D_f$ of the tubular fabric member and that is significantly greater than the diameter $d_1$, and the one of the two cooperating ring stents (LS) which has an uncompressed diameter $d_1$ overlaps the other one of the two cooperating ring stents (S) which has an uncompressed diameter $d_2$ A folded shape may be one in which the compressible ring stent upon compression folds to form curved portions between which there may be at least one resilient hinge portion, and preferably two, spaced apart, resilient hinge portions, each of which resilient hinge portions may be of a shape-set "V"-shape. Alternatively, the folded shape may be one in which the compressible ring stent upon compression folds to form sinusoidal curved portions, such as a "saddle" shape having peak and valley portions in some embodiments. The at least two, spaced apart, resilient hinge portions, which may be of a shape-set "V"-shape, may be located at diametrically opposed positions of the compressible ring stent. The shape-setting of portions of the ring stent into a V-shaped hinge portion may be achieved by heat-setting.

The ring stents used to form the combination of two cooperating ring stents of different configurations may be selected from radially compressible "Z"-stents, or "zig-zag" stents, compressible ring stents, compressible shape-set ring stents, or "saddle" shaped ring stents selected from a range of sizes such that in a combination of two cooperating ring stents of different configurations one such ring stent is a relatively steep "saddle" shaped ring stent (S) and the other ring stent is a relatively less steep "saddle" shaped ring stent (LS).

U.S. Pat. No. 5,035,706 discloses examples of radially compressible "Z"-stents. U.S. Pat. No. 9,993,329 discloses examples of compressible "saddle"-shaped ring stents US2017/0007391 discloses a stent graft of tubular shape with multiple elastic rings intermittently arranged in an axial direction of the tubular shape spanning across both end-parts of the graft, and housed in a delivery sheath with each of the elastic rings being transformed into a "saddle-shape", characterised by provision of a thinner auxiliary elastic wire whose rigidity is lower than that of the elastic rings, and the auxiliary elastic wire is connected, directly or through the graft, to the multiple elastic rings arranged at the end-parts of the graft. That auxiliary elastic wire is an endless annular shape formed from continuously connected first and second wire elements, so that the auxiliary elastic wire endlessly surrounds the graft and has concave portions and convex portions linked by wire elements for tilt stability due to regular spacing, but the auxiliary elastic wire does not cross over the end elastic ring in the graft. Thus the stent graft disclosed there is fundamentally different from that of the present disclosure.

At least one of the two cooperating ring stents of different configurations that is compressible into a folded shape may be a radially compressible Z-stent and the other one of the two cooperating ring stents of different configurations that is compressible into a folded shape may be one which upon compression folds into a "saddle" shape having peak and valley portions. In some embodiments the "saddle"-shaped ring stent is overlapped by the other cooperating ring stent. The cooperating ring stents, although attached to the tubular fabric member at selected discrete points, are free to move relative to one another at cross-over points, thereby enabling the cooperating rings to undergo different levels of deformation necessary to be compactly folded into a delivery catheter and subsequently deployed.

One of the two cooperating ring stents of different configurations that is compressible into a folded shape may be a radially compressible shape-set ring stent comprising hinge portions, such as V-shaped portions, and the other one of the two cooperating ring stents of different configurations that is compressible into a folded shape may be one which upon compression folds into a "saddle" shape having peak and valley portions. In some embodiments the "saddle"-shaped ring stent is outermost and attached to the tubular fabric member so as to cross the other cooperating shape-set ring stent. The cooperating shape-set ring stent may be compacted to a smaller diameter by radial crimping, and is selectively attached to the tubular fabric member such that the points of attachment respectively lie on regions of fabric behind saddle-shaped ring stent peak quartiles. This allows sufficient relative movement between the rings to accommodate the desired levels of deformation necessary for compactly folding for delivery in a catheter and subsequent deployment.

The shape-set ring stent may be selectively attached to the tubular fabric member at points corresponding to fabric regions associated with the "saddle-shaped" ring stent peak portions, the attachment being behind such peak portions. In this way the full deployment of the "saddle-shaped" ring stent permitted within the tubular fabric member is unhindered by the presence of the shape-set ring stent, and the preferred rounded peripheral shape of the "saddle-shaped" ring stent within the tubular fabric member is promoted by the presence of the shape-set ring stent.

In other embodiments at least one of the two cooperating ring stents of different configurations that is compressible into a folded shape may be compressible into a "saddle" shape having peak and valley portions of a relatively steep "saddle" height and the other one of the two cooperating ring stents of different configurations that is compressible into a folded shape may be compressible into a relatively less steep "saddle" shape having peak and valley portions.

A "saddle" shape as used herein and mentioned above refers to a generally circular ring stent formed of a material which is sufficiently resilient as to be reversibly folded into a compactly packaged form in a restraining sleeve or sheath. The ring stent when compressed distorts in a predictable fashion so that it forms folds wherein a first pair of diametrically opposed points on the circumference of the ring are displaced in one axial direction whilst a second pair of diametrically opposed points, centrally located on the circumference between the first pair, are displaced in the opposing axial direction to form a symmetrical "saddle" shape. In any embodiment using such a "saddle" shape ring stent, the configuration may be such that the ring stent folds to form two peaks and two valleys. The "saddle"-shape may be "remembered" by use of a shape-memory material such as Nitinol (a nickel-titanium alloy), or simply held in the desired shape by selective attachment of the "saddle"-shape ring stent to the fabric of the tubular fabric member, for example by suturing peaks and valley portions at least to the fabric.

Such "saddle" shape ring stents may be formed of a continuous loop of resilient material (Nitinol or PEEK or the like strands or fibres) deformable to form a sinusoidal (saddle) shape as described above. The "saddle" shape may be shape-set into a ring stent of resilient material by forming upon a cylindrical or polygonal mandrel.

These "saddle" shaped stents can have a "saddle" height, expressed as a ratio of "saddle" height to graft tubular fabric member open lumen diameter $D_f$, which for a "steep saddle" ring: may be a ratio range of from 1:2.5 up to 1:0.9 (i.e. ring saddle height of 40% up to 110% of fabric tube diameter $D_f$) or from 0 (substantially flat or undeformed planar ring) up to 1:2 (i.e. "saddle"-shaped ring height of 0 up to 50% of graft tubular fabric diameter) for a less steep "saddle" shaped ring stent.

Herein for ease of illustration it is intended to distinguish the different ring stents used in the combination of two cooperating ring stents of different configurations, referring to those compressible ring stents that adopt a "saddle" shape when folded as "saddle"-shape ring stents, and those other shape-set ring stents used in the combination of two cooperating ring stents of different configurations, such as those formed with shape set parts such as flexible hinge portions or discrete sinusoidal portions will be referred to as simply "shape-set" ring stents generally, or specifically described as having heat-set hinge portions for example according to context. Additionally, ring stents which are formed from straight-set wire into undeformed circular stents will be referred to simply as "ring stents". Each ring stent may be formed from winding together multiple wire filament strands, say from 2 to 120 or more strands. Any diameter wire which maintains the required resilience can be used. Suitable diameters for the wire can be selected from a range of 0.05 mm to 2 mm, for example 0.5 mm to 1 mm.

In embodiments employing "saddle" shape ring stents attached at least at one of the first and second ends of the tubular fabric member to form the combination of two cooperating ring stents of different configurations, one of the "saddle" shape ring stents has a "saddle" height that is considered as "steep" i.e. within the range of 40-110% of the diameter of the tubular fabric member $D_f$ and the other one has a "saddle" height that is considered as "less steep" i.e. within the range of from 0-50% of the diameter of the tubular fabric member $D_f$ which ranges are representative and non-limiting guidelines since it is the relative difference in the configuration of the folded or compressed ring stents forming the combination of the two cooperating ring stents which is effective.

In other embodiments, one of the two cooperating ring stents of different configurations that is compressible into a folded shape may be a shape-set ring stent having at least one "V"-shaped flexible hinge portion, optionally a shape-set ring stent may have more than one "V"-shaped flexible hinge portion, and otherwise the shape-set ring stent may have curvilinear portions on either side of the at least one shape set "V"-shaped portion, or between the more than one "V"-shaped flexible hinge portions. Where two "V"-shaped flexible hinge portions are formed in the shape-set ring stent, they may be positioned at diametrically opposite positions of the shape-set ring stent.

In embodiments, at least one of the two cooperating ring stents of different configurations that is compressible into a folded shape is positioned at least in part within the other one of the two cooperating ring stents of different configurations that is compressible into a folded shape.

In embodiments, the shape-set ring stent may be compressible radially into a folded shape and expansible radially within the open lumen diameter $D_f$ of the tubular fabric member, and is located on an end of the tubular fabric member such that a portion of the shape-set ring stent extends beyond the length $L_f$ of the tubular fabric member and is not covered by fabric of the tubular fabric member, i.e. that portion is exposed as bare stent or optionally covered or coated with material to render the exposed portion less traumatic to the contacted natural vessel wall during pulsatile flow cycling.

In embodiments, the "V"-shaped portions of the shape-set ring lie within the length $L_f$ of the tubular fabric member and the curvilinear portions extend beyond the length $L_f$ of the tubular fabric member.

In embodiments, the shape-set ring stent is positioned at least in part within a ring stent which is compressible into a "saddle" shape having peak and valley portions.

In embodiments, the tubular fabric member has a substantially circular perimeter at each of the first and second ends, and the ring stent which is compressible into a "saddle" shape is attached to the fabric of the tubular fabric member at multiple points around the perimeter of one of the first and second ends, and the shape-set ring stent is selectively attached to parts of the fabric of the tubular fabric member to allow the ring stent which is compressible into a "saddle" shape having peak and valley portions to slide across the shape-set ring stent during compaction and deployment (folding and unfolding).

In embodiments, each of the two cooperating ring stents of different configurations that is compressible into a folded shape may be compressible into a "saddle" shape having peak and valley portions, wherein one of the two cooperating ring stents has an uncompressed diameter $d_1$ that is greater than or equal to the open lumen diameter $D_f$ of the tubular fabric member and the other one of the two cooperating ring stents has an uncompressed diameter $d_2$ that is greater than the open lumen diameter $D_f$ of the tubular fabric member and that is significantly greater than the diameter $d_1$, and the one of the two cooperating ring stents which has an uncompressed diameter $d_1$ may overlap the other one of the two cooperating ring stents which has an uncompressed diameter $d_2$ so as to constrain the latter without being attached to it. The combination of two cooperating ring stents of different configurations may be held in a cooperating relationship by selective attachment of each of two cooperating ring stents to the fabric of the tubular fabric member. Alternatively, the cooperating relationship can also include selective attachment between each of two cooperating ring stents at cross-over points in the curvilinear region between the "peaks" and "valleys" of a steep "saddle"-shaped ring stent.

In embodiments, a deployed flat ring or shallower height "saddle" ring stent provides a radial constraint on the steep height "saddle" ring stent so that in use for deployment within a damaged vessel, a stent graft prosthetic device will only open during deployment to a limited extent determined by the overlying flat (planar) ring or less steep "saddle" ring stent which provides constraint and mitigates the potential problem of long term over-dilation of the device within the damaged vessel.

Additionally the overlapping stent configuration proposed herein provides for good apposition of the ring stents within the vessel walls to provide sufficient sealing for the intended purpose within the vessel being treated because the inner steep height "saddle" ring stent urges the overlapping outer flat or shallower height "saddle" ring stent against the vessel wall.

Similar advantages are achievable in other combinations as disclosed herein. Use of a shape-set "hinged" ring stent in combination with a "saddle" shaped end ring stent configured as the overlying outer ring stent slidably crossing portions of the shape-set ring stent provides for deployment wherein the shape-set ring stent expands radially, and perpendicularly to the walls of the vessel being repaired which radial expansion urges the "saddle" shaped end ring stent into a desired round cross-sectional shape whilst retaining a shallower "saddle" shape in comparison with its compacted steep "saddle" shape. Thus the internal shape-set ring prevents the outer "saddle" shaped end ring stent from distorting into the so-called "petal"-shape or "ovalling" deformation which may be recognised when only an end ring of a "saddle" shape is deployed. Such "ovalling" is undesirable since it may lead to over-dilation of the vessel (risking excessive strains in the natural vessel walls) and potential prosthetic device migration from the repair treatment site after long term implantation.

In all embodiments, the ring stents are further compressible to a compact configuration for delivery, for example within a sheath which restrains the compressed compact ring stents until a release at a treatment site is required. It is known to use removable sheaths to constrain a prosthetic device in a compact configuration for delivery purposes. Such use is described for example in US2011196472 (A1), and US2013178925 (A1).

The ring stents described herein enable a stent graft formed from a tubular fabric material to be supported in an open lumen configuration by self-expansion of the ring stents after a delivery constraint such as a sheath is removed.

In embodiments, at least one of the first and second ends of the tubular fabric member may be supported by a combination of two cooperating ring stents of different configurations, and each one of the two cooperating ring stents of different configurations is compressible into a folded shape, and the stent graft prosthesis may be optionally supported throughout its length by further stents, none of which optional further stents contact either one of the two cooperating ring stents of different configurations in the combination of two cooperating ring stents of different configurations when the stent graft prosthesis is in its deployed form in a natural vessel.

In embodiments a stent graft prosthesis may have at least one, optionally each one, of the first and second ends of the tubular fabric member supported by a combination of two cooperating ring stents of different configurations, and each one of the two cooperating ring stents of different configurations is compressible into a folded "saddle"-shape wherein one ring stent of the combination is of a steeper "saddle"-shape than the other one ring stent of the combination of two cooperating ring stents of different configurations.

In embodiments, one of the two cooperating ring stents of different configurations at each of the first and second ends of the tubular fabric member may have projecting portions of stent extending beyond the fabric of the tubular fabric member, which projecting portions may be bare metal curvilinear portions exposed beyond the length $L_f$ of the tubular fabric member. Alternatively, the projecting portions may be optionally covered or coated with material to render the exposed portion less traumatic to the contacted natural vessel wall when the stent graft prosthesis is deployed within the lumen of a natural vessel.

BRIEF DESCRIPTION OF THE DRAWINGS

Preferred embodiments will now be described, by way of example only, with reference to the following drawings.

DESCRIPTION OF EMBODIMENTS

Figure 1:
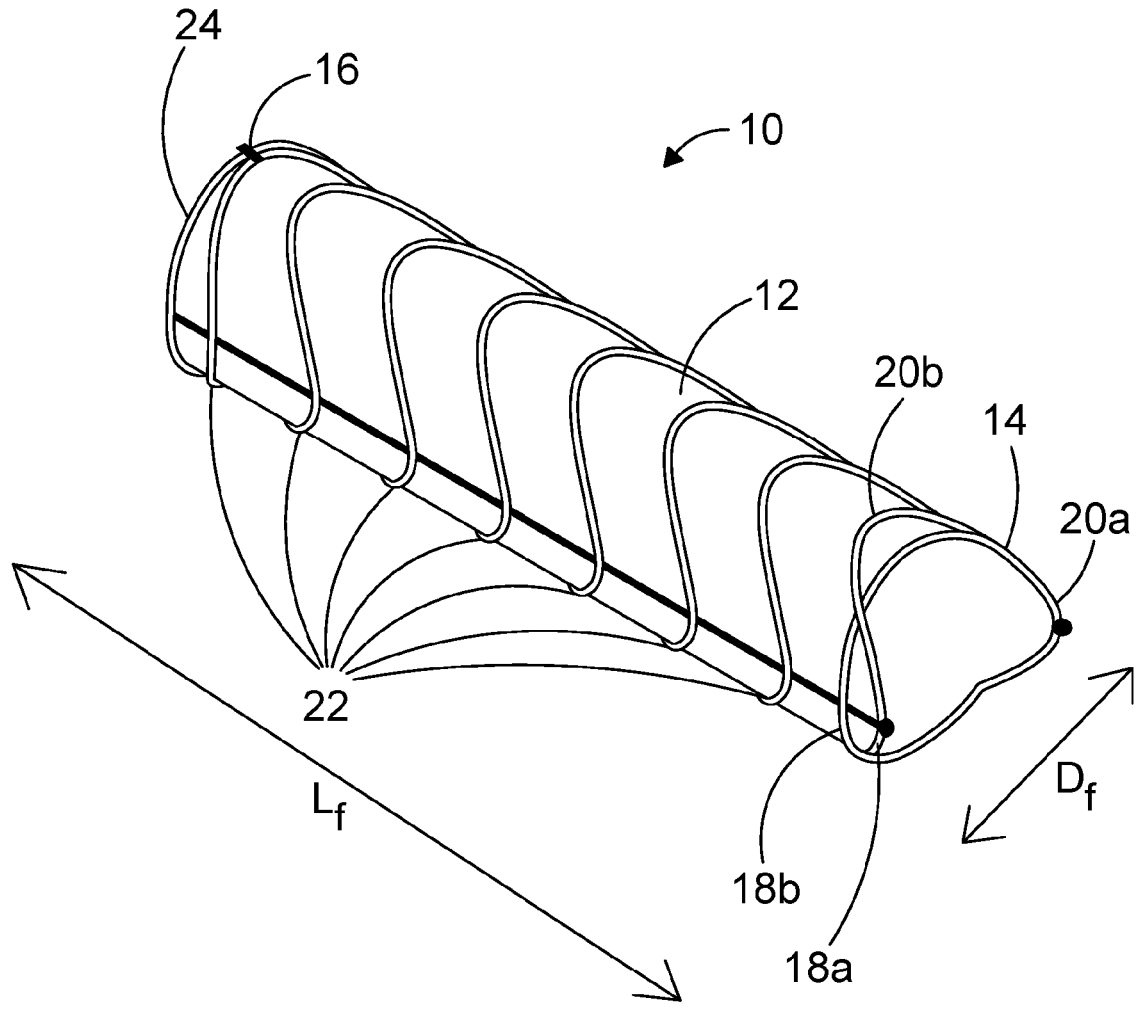
FIG. 1 shows a perspective view of a stent graft prosthesis according to a first embodiment.
Figure 2A:
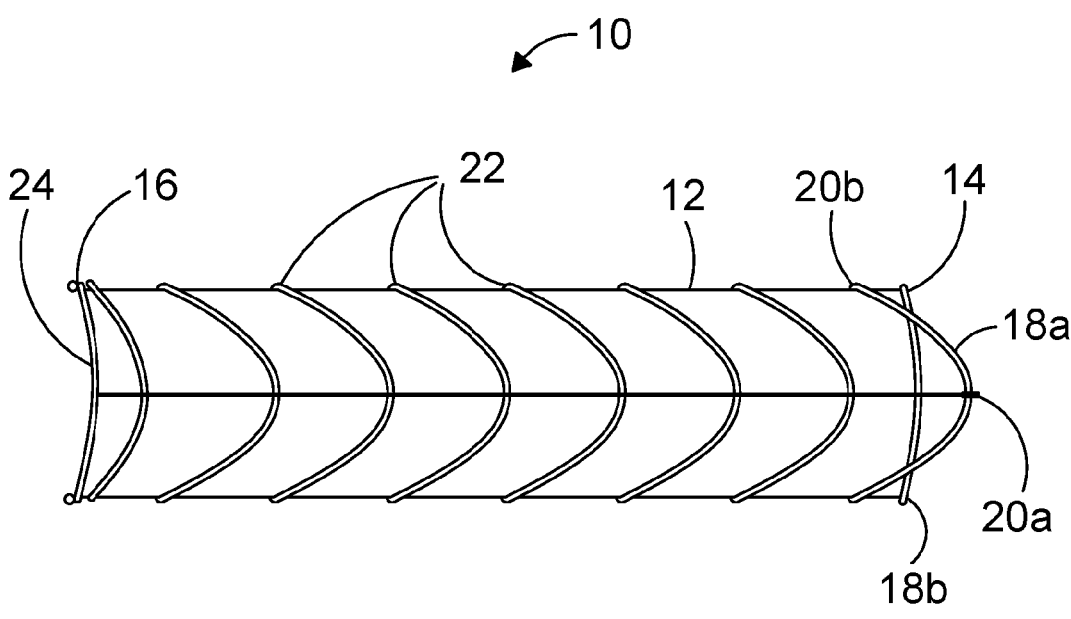
FIGS. 2A and 2B show side views of the stent graft prosthesis of FIG. 1.
Figure 2B:
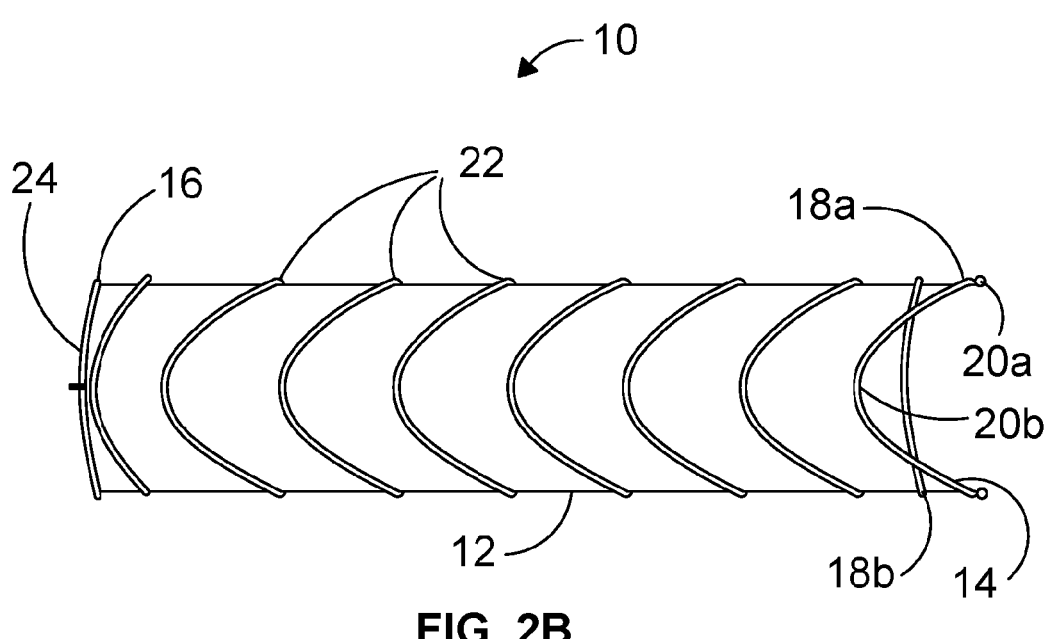

With reference to FIGS. 1, 2A and 2B there is shown a stent graft prosthesis 10 according to a first embodiment. As shown the stent graft prosthesis 10 includes a tubular fabric member 12, which has a first end 14, and a second end 16. A length ($L_f$) of the tubular fabric member 12 extends between the first and second ends 14, 16. The length $L_f$ being the longest dimension of continuous tubular fabric aligned with the longitudinal axis of the tubular fabric member 12. The tubular fabric member 12 has an open lumen diameter $D_f$.

In the depicted example, the first end 14 of the tubular fabric member 12 is supported by a combination of two cooperating ring stents 18a, 18b. Each of these stents is compressible into a folded shape. The cooperating ring stents comprise first ring stent 18a and second ring stent 18b. Both of the first and second ring stents 18a, 18b in the depicted example are "saddle" shaped stents, which have peak and valley portions 20a, 20b. Each of the first and second ring stents 18a, 18b has a "saddle height" as defined above.

As shown, the first and second ring stents 18a, 18b are located on the exterior of the tubular fabric member 12, and each of the first and second ring stents 18a, 18b has an unfolded diameter that exceeds the open lumen diameter $D_f$ of the tubular fabric member 12, as best shown in FIG. 1 which provides for biasing the first end 14 of the tubular fabric member 12 to open when deployed. As shown, the first ring stent 18a is located at least partially within the second ring stent 18b. Thus deployment of the ring stent combination 18a, 18b supports the first end 14 of the tubular fabric member and facilitates sealing with a healthy portion of natural vessel when deployed therein.

As shown in this depicted example, the first and second ring stents 18a, 18b have different configurations. For example, as shown, the deployed diameter of the second ring stent 18b exceeds that of the first ring stent 18a. However, when unfolded and not attached to the tubular fabric member 12 it will be understood that the first ring stent 18a has a greater diameter than the second ring stent 18b causing the first ring stent 18a to adopt a steeper "saddle" height when constrained as illustrated within the second ring stent 18b and tubular fabric member 12. Also, the second ring stent 18b has a much lower "saddle" height (less steep) than that of the first ring stent 18a.

In an alternative example, the second ring stent 18b is substituted by a ring stent which deploys from a compacted folded "saddle" shaped stent to a "flat" circular ring stent which crosses over the steeper "saddle"-shaped ring 18a at four points in the region between the "peaks" and "valleys" of the steep "saddle"-shaped ring stent 18a.

Referring again to FIG. 1, each of the first and second ring stents 18a, 18b is fixed to the tubular fabric member 12, for example with sutures. The manner in which the first and second ring stents 18a, 18b are fixed to the tubular fabric member 12 may be the same as shown with respect to the second embodiment in FIGS. 3A and 3B. Suitable materials for the sutures include nylon, polypropylene, silk and polyester, in braided or monofilament form. The first and second ring stents 18a, 18b may be balloon-expandable (e.g. a PALMAZ stent made of rigid stainless steel wire), but could also be self-expandable and formed of a shape memory material, such as nitinol (a nickel-titanium alloy).

The stent graft prosthesis 10 is supported throughout its length by further stents 22. However, as depicted, none of these stents 22 are in contact with each of the first and second ring stents 18a, 18b. The further stents 22 in this embodiment are also "saddle" shaped stents with peak and valley portions. In the depicted example, the cooperating ring stents 18a, 18b are provided at the first end 14 of the tubular fabric member 12, and a circular end stent 24 is provided at the second end 16 of the tubular fabric member 12. However, alternatively, a combination of cooperating ring stents 18a, 18b may also be provided at the second end 16 of the tubular fabric member 12. The cooperating ring stents 18a, 18b act to support the first end of the tubular fabric member radially.

Figures 3A, 3B, 3C:
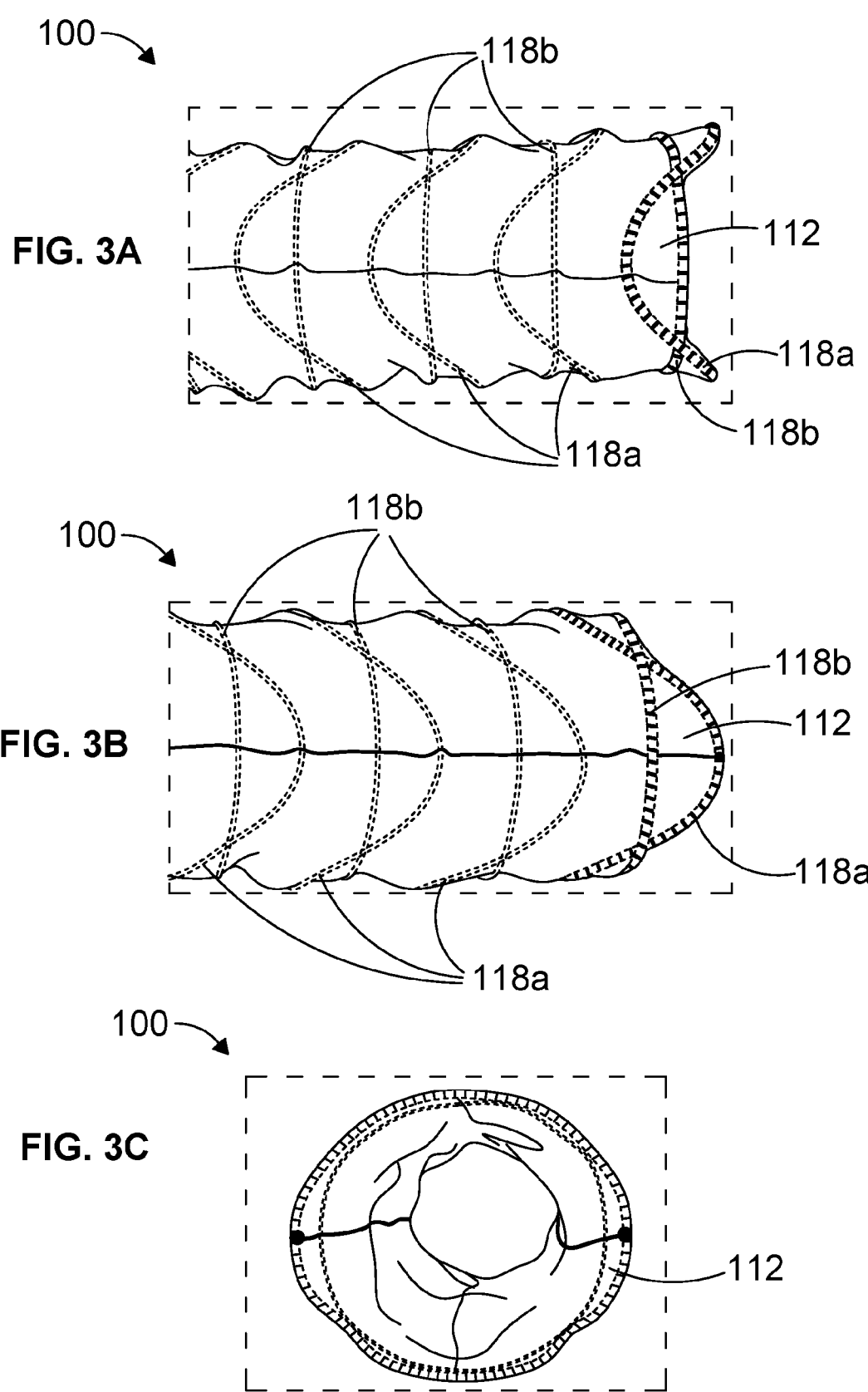
FIGS. 3A, 3B and 3C show a stent graft prosthesis according to a second embodiment.

FIGS. 3A, 3B and 3C illustrate a second embodiment of a prosthesis 100 according to the present invention. The second embodiment is a modified version of the first embodiment. In this embodiment, the further stents which support the tubular fabric member 112 throughout its length comprise a plurality of combinations of cooperating ring stents 118a, 118b spaced apart along the length of the tubular fabric member.

Figures 4A, 4B, 4C:
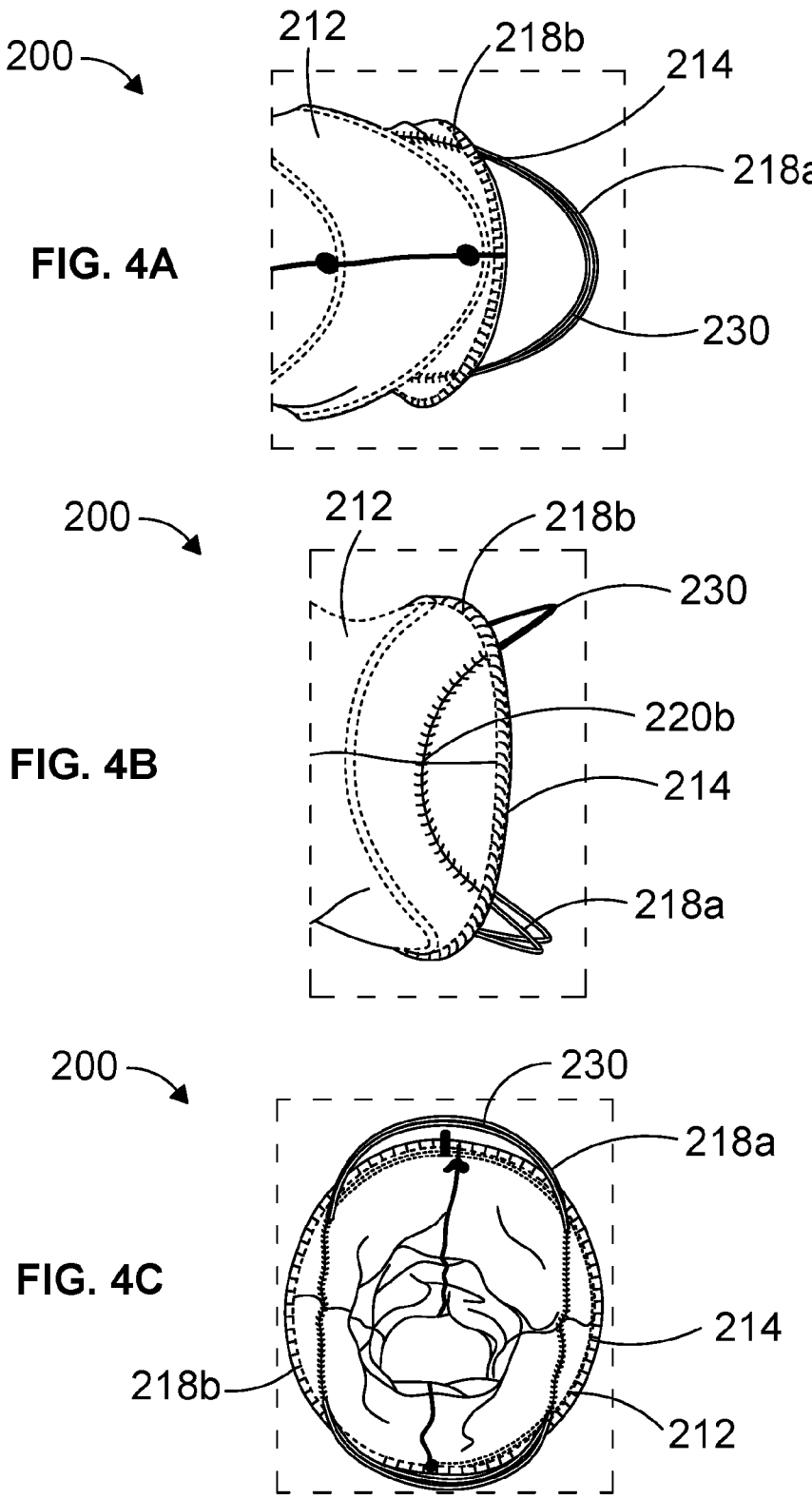
FIGS. 4A, 4B and 4C show a stent graft prosthesis according to a third embodiment.

FIGS. 4A, 4B and 4C illustrate a third embodiment of a prosthesis 200 according to the present invention. The third embodiment is a modified version of the first embodiment. Here, like the first embodiment, both the first and second ring stents 218a, 218b are "saddle shaped" stents. In this embodiment, the first ring stent 218a is located at a first end 214 of a tubular fabric member 212 and inside the second ring stent 218b such that a portion 230 of the first ring stent 218a extends beyond the length of the tubular fabric member 212. Optionally, the first ring stent 218a is formed from metal, and shape-set into a "saddle" shape on a cylindrical or polygonal mandrel. Otherwise the desired "saddle" may be formed by ring folding manipulation and stitching the "saddle" shape to the fabric of the tubular fabric member 212 at selected locations. As best shown in FIG. 4B only the valley portion 220b of the first ring stent is fixed to the interior of the tubular fabric member 212, and the portion 230 of the first ring stent which extends beyond the tubular fabric member 212 is a peak portion of the first ring stent 218a.

Figure 5:
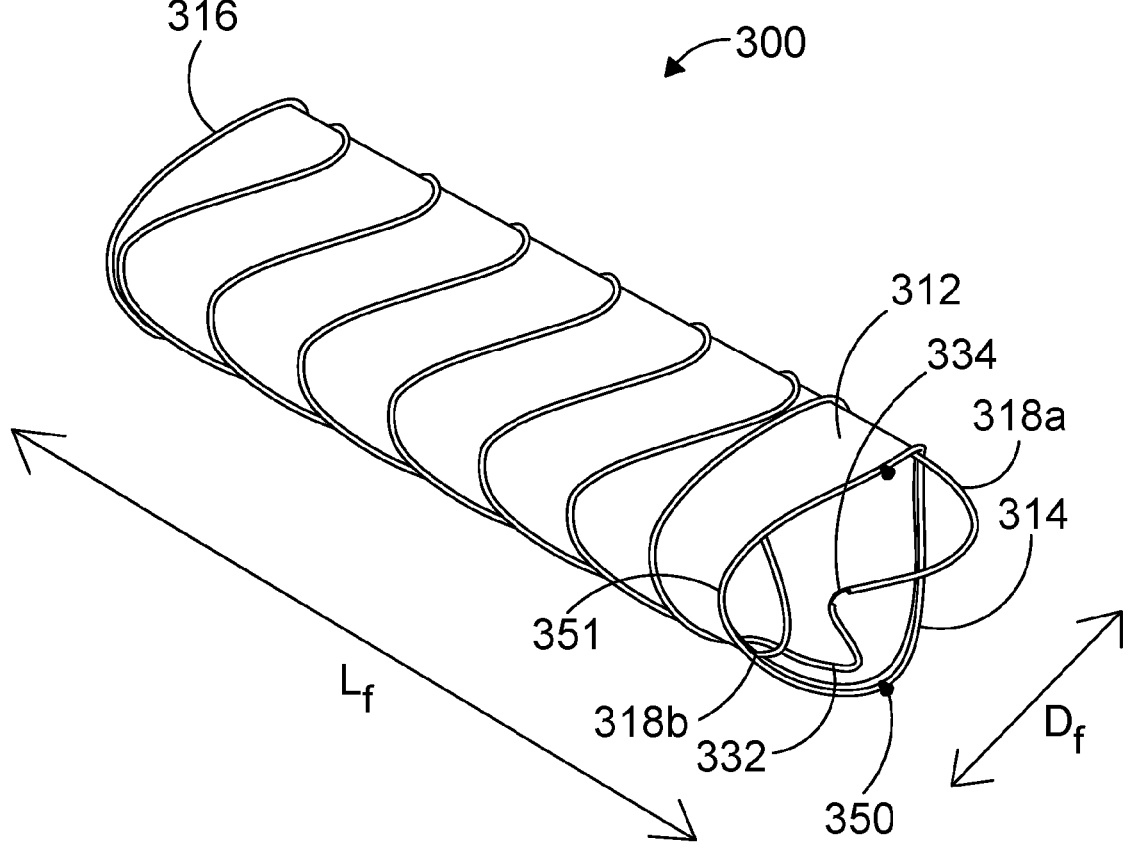
FIG. 5 shows a perspective view of a stent graft prosthesis according to a fourth embodiment.
Figure 6A:
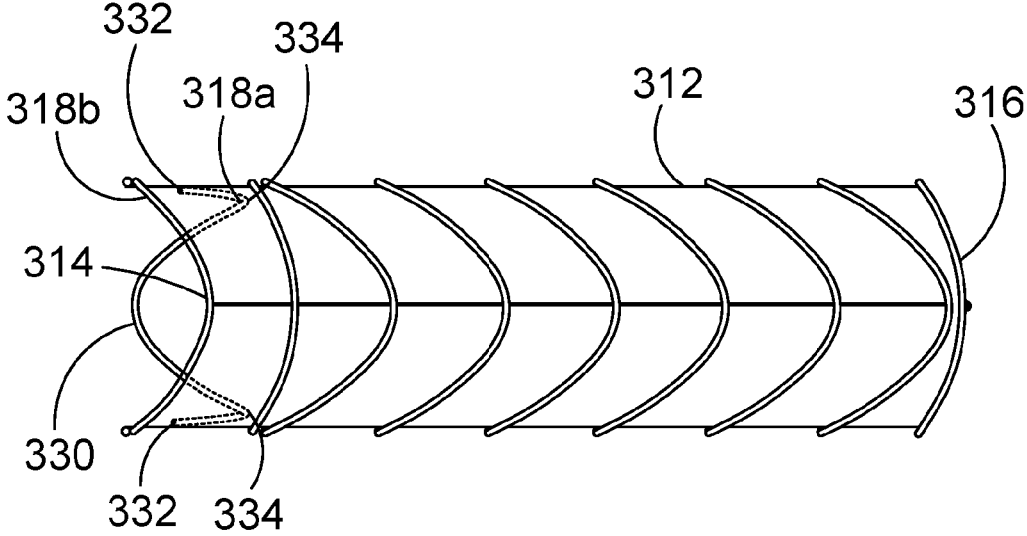
FIGS. 6A and 6B show the stent graft prosthesis of FIG. 5.
Figure 6B:
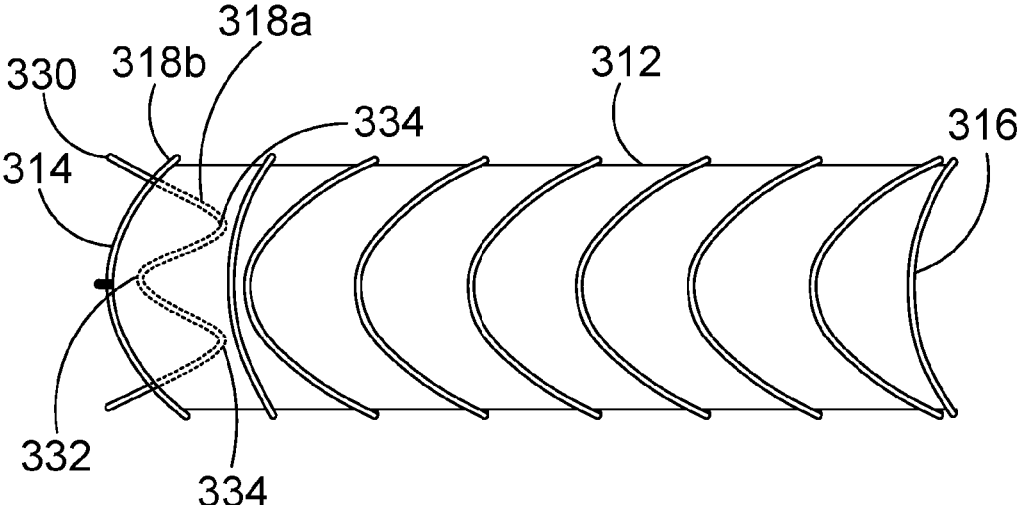

With reference to FIGS. 5, 6A and 6B, there is shown a prosthesis 300 according to a fourth embodiment of the present invention. Like the first embodiment, the stent graft prosthesis 300 comprises a tubular fabric member 312 having first and second ends 314, 316, and a combination of two cooperating ring stents 318a, 318b of different configurations. Further the tubular fabric member 312 has an open lumen diameter $D_f$ as in the first embodiment. However, the combination of two cooperating ring stents 318a, 318b is arranged differently with respect to the first embodiment, and is described below.

The cooperating ring stents comprise first and second ring stents 318a, 318b. The first ring stent 318a is a shape-set ring stent comprising at least one "V"-shaped portion 332, and the second ring stent 318b is a "saddle"-shaped ring stent with "peak" and "valley" portions 350, 351. The first ring stent 318a is located inside the second ring stent and has a diameter which exceeds the open lumen diameter $D_f$. As shown, the shape-set stent 318a comprises two "V"-shaped hinge portions 332, which are separated from one another by curvilinear portions 334 such that they are presented in diametrically opposed positions within the open lumen diameter $D_f$ and attached to the fabric of the tubular fabric member 312. Further, the shape-set stent 318a comprises a portion 330 which extends beyond the tubular fabric member 312.

In the embodiment of FIGS. 5, 6A and 6B, the combination of cooperating ring stents 318a, 318b is provided at the first end 314 of the tubular fabric member 312. The first ring stent 318a (shape-set) is fixed to the inner surface of the tubular fabric member 312, and the second ring stent 318b ("saddle"-shape) is fixed around the perimeter of the first end 314 of the tubular fabric member 312. Each of the first and second ring stents 318a, 318b is fixed to the tubular fabric member 312 with sutures such that the first ring stent 318a can slide over the second ring stent 318b when necessary, for example during folding to compact the stent graft prosthesis 300 for delivery into a lumen of a natural vessel, or when deploying the stent graft prosthesis 300 in a lumen of a natural vessel. This relative sliding motion is achievable where the first ring stent 318a (shape-set) is fixed to the inner surface of the tubular fabric member 312 by the "V"-shaped hinge portions 332 in the vicinity of a peak portion 350. Therefore the cooperating ring stents 318a, 318b are separately fixed to the tubular fabric member 312 and can be compactly folded and subsequently opened for deployment with independent relative movement at the same time.

Figure 7:
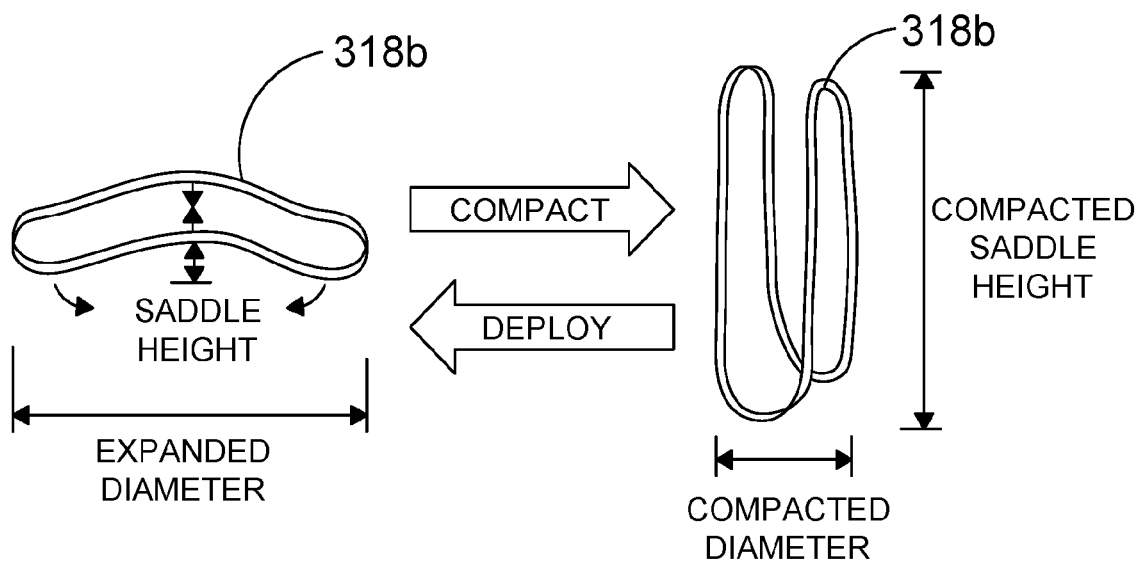
FIG. 7 shows a stent such as used in the stent graft prosthesis of FIG. 5 illustrating schematically folding of the ring stent to form a "saddle"-shape stent in the alternative deployed and compacted configurations.

FIG. 7 shows the second ring stent 318b in compacted and deployed states. As shown, in the deployed state, the "saddle" diameter of the second ring stent 318b is much greater than in the compacted state. Further, the "saddle" height of the second ring stent 318b is much greater in the compacted state with respect to the deployed state.

Figure 8:
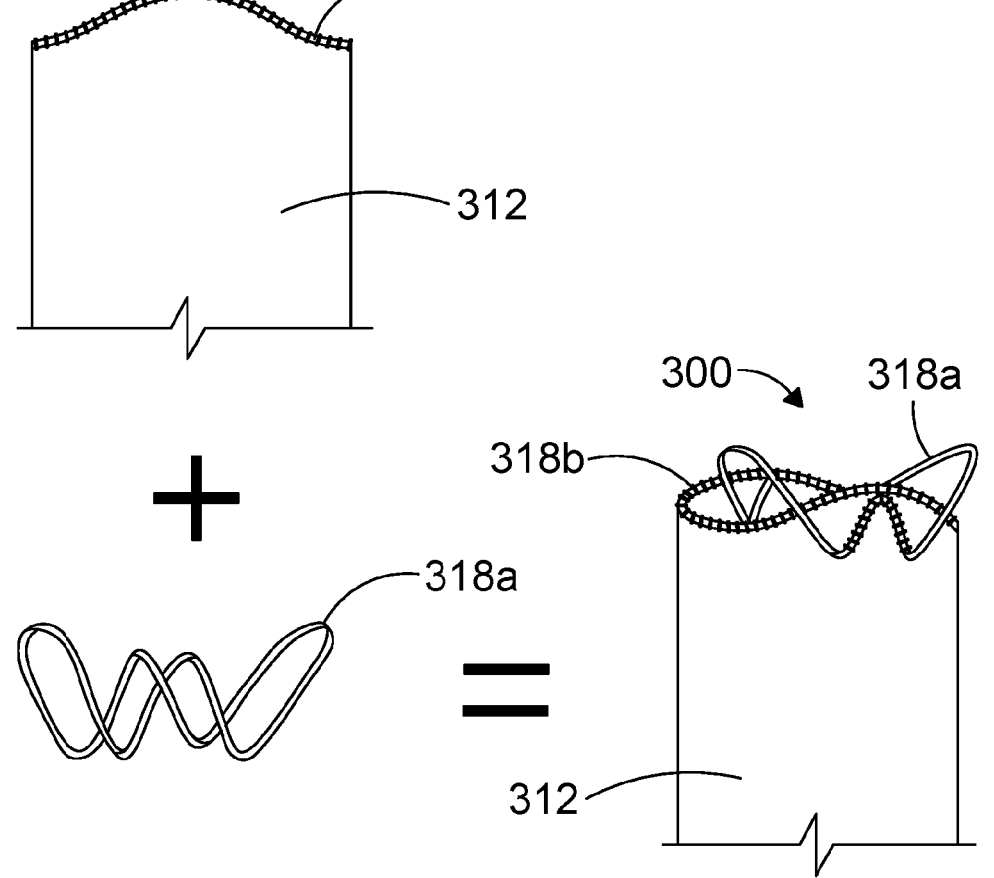
FIG. 8 illustrates schematically a side view of an end of a tubular fabric member with a first ring stent such as the "saddle"-shape stent of FIG. 7 attached thereto, and a second ring stent such as the shape-set ring stent of the stent graft prosthesis of FIG. 5, which in combination form the open lumen end support for the stent graft prosthesis of FIG. 5.

FIG. 8 shows the tubular fabric member 312 with the second ring stent 318b attached thereto, and the first ring stent 318a separate from the tubular fabric member 312. FIG. 8 also shows the stent graft prosthesis 300, which is formed when the first ring stent 318a is fixed to the inner surface of the tubular fabric member 312 such that it is located within the second ring stent 318b. As mentioned above the first ring stent 318a (shape-set) is fixed only to the inner surface of the tubular fabric member 312 by the "V"-shaped hinge portions 332 in the vicinity of a peak portion 350 so that independent relative motion is possible with one stent sliding across contact points with the other.

Figure 9:
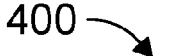
FIG. 9 shows a stent graft prosthesis according to a fifth embodiment.
Figure 9:
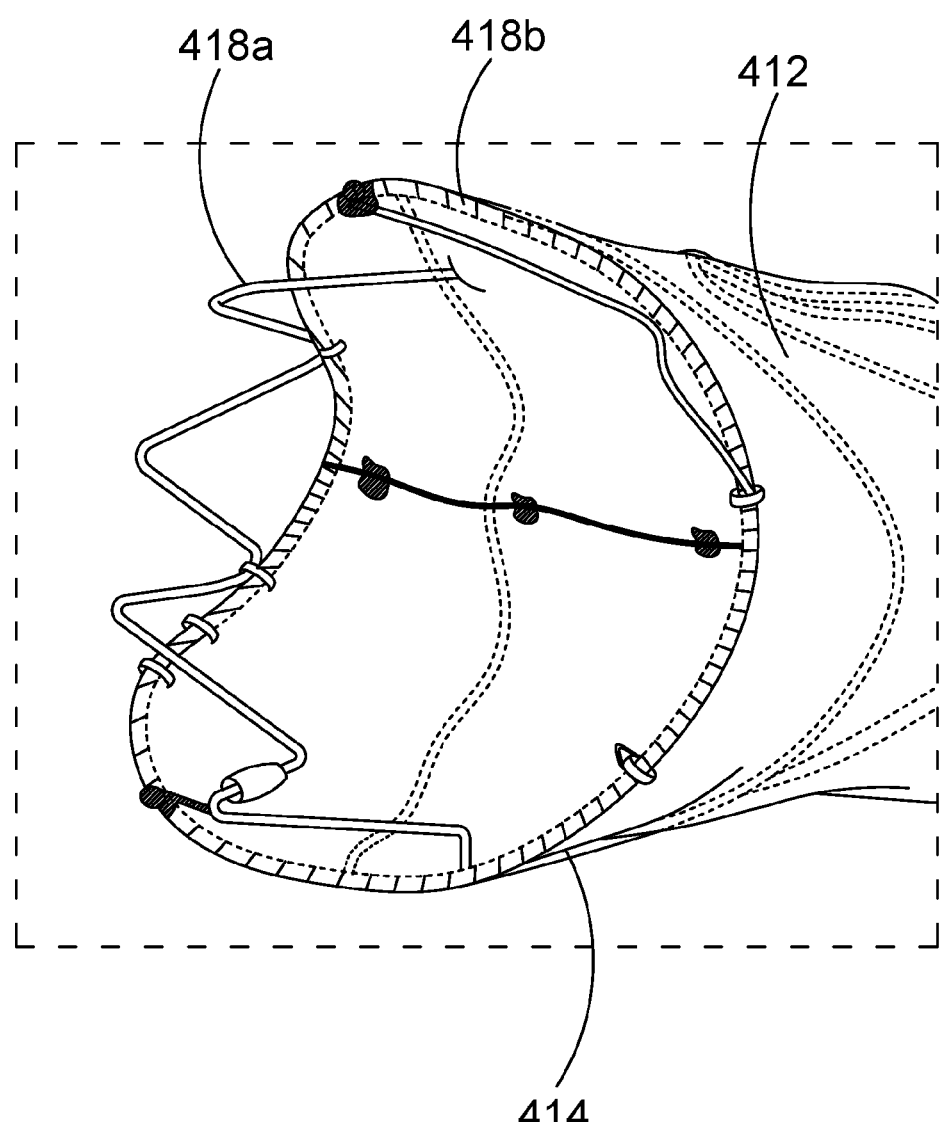

FIG. 9 shows an end part of a stent graft prosthesis 400 according to a fifth embodiment of the present invention. The fifth embodiment is a modified version of the first embodiment. Here, like the first embodiment, the stent graft prosthesis 400 comprises a tubular fabric member 412 having first and second ends supported by a combination of ring stents having different configurations. For the purposes of illustration a first end 414 of the tubular fabric member 412 is held open by a combination of two cooperating first and second ring stents 418a, 418b of different configurations which function similar to the combination of the first embodiment described above. The ring stent 418b, which is fixed to the outer surface of the tubular fabric member 412, is a "saddle" shaped stent. However, in contrast to the first embodiment, the first ring stent 418a, which is located within the second ring stent, has multiple "V" shaped hinge portions connected together and can be referred to as a "Z"-shaped stent which compacts and expands radially. Z-shaped stents are known per se to the skilled person. As in the embodiment of FIGS. 5, 6 and 8, the attachment of the Z-shaped stent is by fastening a "V"-shaped hinge portion to the inner surface of the tubular fabric member 412 only in the vicinity of a peak portion of the second ring stent 418b so that independent relative motion is possible with one stent sliding across contact points with the other stent.

Figure 10:
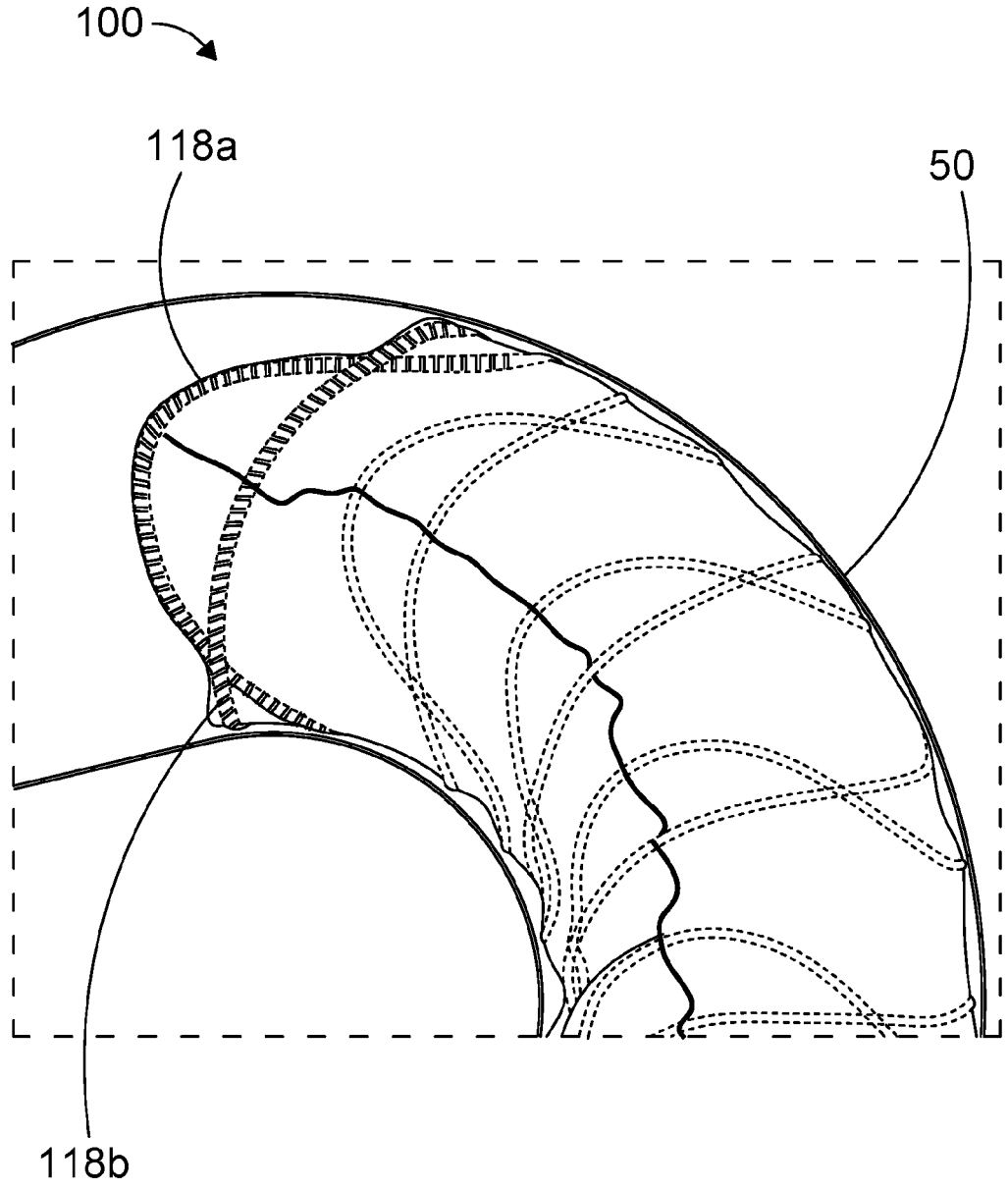
FIG. 10 shows how the sent graft prosthesis of FIG. 3A may be deployed within a vessel.

FIG. 10 shows the stent graft prosthesis 100 deployed within a transparent curved tube in a test device in order to simulate performance in a curved natural vessel 50. When the stent graft prosthesis 100 is deployed from a compacted state within the vessel 50, the first ring stent 118a opens without hindrance from the second ring stent 118b on account of being able to slide at contact points due to selective fastening of the respective ring stents to the fabric of the tubular fabric member 112. The second ring stent 118b acts to constrain the first ring stent 118a such that the tubular fabric member 112 has, and retains, a circular cross-section. This ensures a good radial fit is formed between the vessel and the stent graft prosthesis 100 when the stent graft prosthesis is deployed inside the vessel. This means that problems observed in use of a single "saddle"-shaped stent such as "ovaling" of the stent graft prosthesis 100 does not occur, thereby ensuring long-term radial stability of the position of the stent graft prosthesis within the vessel 50. It is found that use of a steep "saddle"-shape ring stent is beneficial for stability and radial opening (for perpendicular deployment), whilst use of a less steep (or circular) ring stent is beneficial for achieving sealing apposition.

Figure 11A:
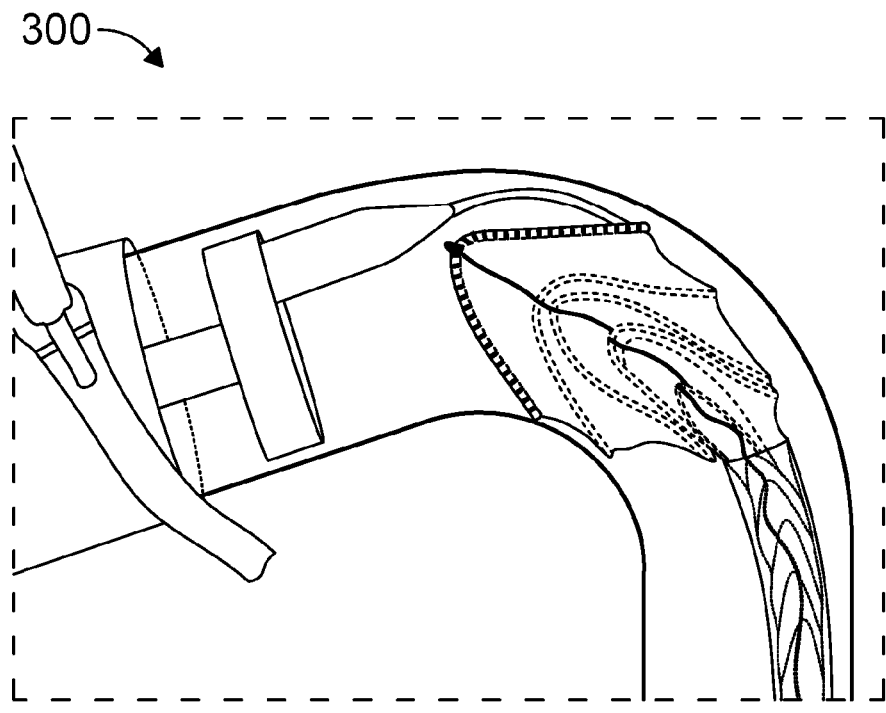
FIGS. 11A and 11B show a test device for evaluating how the stent graft prosthesis of FIG. 5 may be respectively introduced to an arched lumen and deployed within the arched lumen in order to predict performance in a procedure to repair the aortic arch or similar curved natural vessel.
Figure 11B:
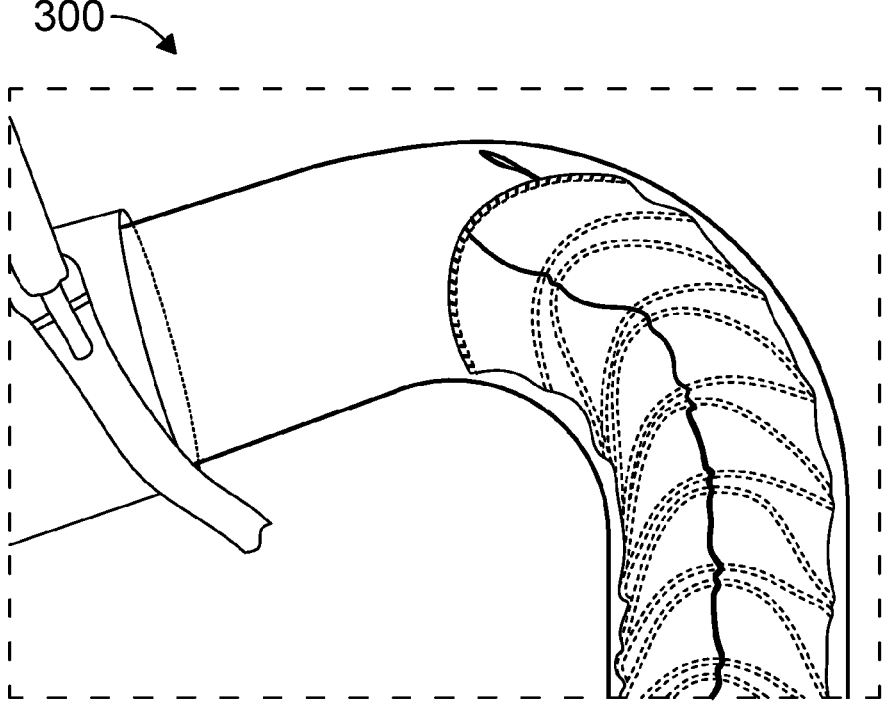
Figure 12A:
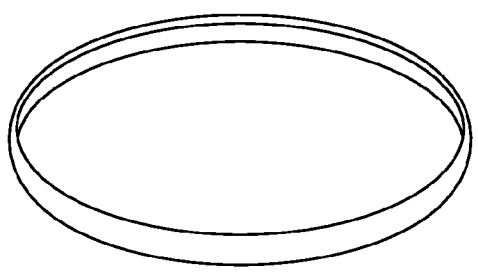
FIG. 12A shows a perspective view of a ring stent which has not been shaped or folded so that its circumference lies in a single plane (planar ring)
Figure 12B:
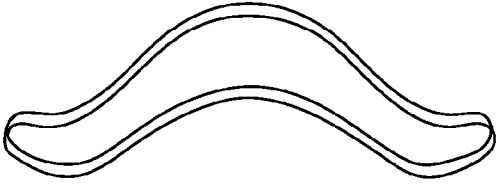
FIG. 12B shows a perspective view of a ring stent of a "saddle"-shape.
Figure 12C:
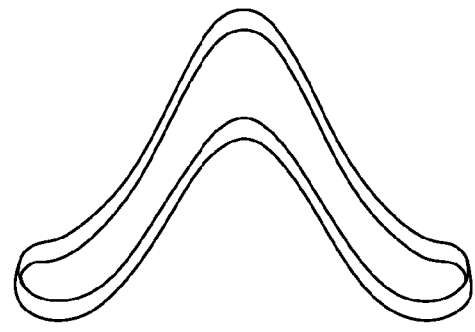
FIG. 12C shows a perspective view of a ring stent of a steep "saddle"-shape.

FIGS. 11A and 11B show sequential steps of the method of deployment of the stent graft prosthesis 300 of the embodiment of FIGS. 5, 6A and 6B which is observable in a transparent tube of a test device which has a scale for determining angular changes of the proximal end of a tubular graft prosthesis as it is introduced to the arched portion and allowing clear visibility of the extent of tube surface contact with the proximal end of the tubular graft prosthesis, and which simulates introduction of the tubular graft prosthesis to a natural vessel lumen such as the lumen of the aortic arch.

It has been observed in patients undergoing thoracic endovascular aortic repair that structural changes and incomplete endograft apposition to the aortic arch may be manifested. This type of problem has been referred to as the "bird-beaking" effect.

The present disclosure addresses such problems by providing various embodiments of combinations of two cooperating ring stents of different configurations whose attributes work together to provide improved solutions for obviating or mitigating these problems.

In use of an embodiment as disclosed herein, the proximal shape-set ring makes the proximal end of the tubular graft prosthetic device self-centering within the curved lumen of the natural vessel as it is unsheathed from its compact delivery configuration, which action provides for the proximal ring sealing stent to achieve good apposition and stability without 'bird-beaking'. This is achievable readily with the disclosed stent combination as the shape-set stent emerges from the sheath first and contacts the outer wall of the natural vessel to be repaired. As it opens up and reacts against the vessel walls, the shape-set stent pushes the proximal end of the tubular graft prosthetic device to deploy centrally within the lumen of the natural vessel. This means that the other ring stent required for sealing is centrally positioned in the lumen with a stable symmetrical "saddle"-shape. This ensures that the proximal end of the tubular graft prosthetic device has good apposition to the vessel wall around its circumference, with no bird-beaking at the inner curve of the arched portion.

In an embodiment of a tubular graft prosthetic device a ring stent is attached around its perimeter to the circular end fabric of the tubular graft member to form a stent graft that can be compactly packaged within a delivery sheath to change the diameter of the tubular graft prosthetic device to a lesser diameter by folding of the ring stent into a steep saddle shape having "peak" and "valley" portions. Subsequent removal of the delivery sheath leads to opening of the folded "saddle"-ring from the compact steep "saddle"-shape to a less steep "saddle"-shape or circular ring stent depending upon the constraints imposed by the contacted wall of the natural vessel into which the tubular graft prosthetic device is delivered. Whereas that much is "normal" procedure, the effect of introducing a shape-set ring stent in combination with the "saddle"-shape stent is significant. In a disclosed embodiment, that shape-set ring stent has two "V"-shaped hinge portions connected by curvilinear portions, such that the "V"-shaped hinge portions are diametrically disposed on the fabric wall of the tubular graft member that has a generally cylindrical form. The shape-set stent when compactly forced into a delivery configuration changes from one diameter to another lesser diameter by radial deformation. The shape-set ring stent is attached by the two opposite "V"-shaped hinge portions to the graft fabric in the regions behind the 2 ring peak quartiles, and is not attached to the graft fabric in the regions of the 2 ring valley quartiles. When attached by stitching the divergent limbs of the "V"-shaped hinge portions to the fabric, the shape-set stent crosses the ring stent at (at least) 4 points, each point being on a curvilinear portion between a peak and a valley of the "saddle"-shape ring stent. The "saddle"-shape ring stent is free to slide on the shape-set stent where these cross points occur. This arrangement allows the stent graft to be compacted or expanded, despite the different deformation modes of the stents attached to it In an embodiment the shape-set ring stent has a geometry comprising two "hinge" elements (each with one peak portion and two valley portions) located on the ring stent such that there is a maximum width dimension (diameter) between the locations, and two curved portions between those opposite locations and extending in the proximal direction. The "hinge" portions are used for attachment to the fabric in the regions behind the ring peak quartiles, with each hinge peak located behind a ring peak. The curved portions are exposed beyond the end of the graft fabric above the ring valley quartiles to form 'bare metal' stent elements in these regions. This geometry, with curved bare metal stents i.e. uncovered by the graft fabric, enables atraumatic contact with a wall surface of the natural vessel being repaired. The exposed stent elements may be optionally covered or coated with material, stitching or otherwise treated to mitigate contact trauma.

In embodiments each one of the two cooperating ring stents of different configurations can be conveniently made from the same materials, for example made from the same memory material such as Nitinol (NiTi alloy) wire.

The following advantages are provided by embodiments of the disclosed stent graft prosthesis of the present invention:

1. When the presently disclosed stent graft prosthesis is deployed at a target treatment site within a lumen of a vessel, the cooperating ring stents provide stable positioning within the vessel, even without the aid of delivery system positioning mechanisms.
2. The combination of two ring stents instead of just a single ring allows that a second ring stent provides a constraint on the first ring stent in terms of how far it can open up (radially) during deployment. This means that over time, as the vessel remodels under the chronic outward force of the self-expanding stents, the stent graft prosthesis will only open up as far as the second ring stent allows, thereby avoiding problems of long-term vessel overdilation.
3. The arrangement of cooperating stents of the present invention also results in good apposition of the stents with the vessel walls, as the first ring stent applies a radial force to hold the second ring stent against the vessel wall.
4. The cooperating ring stents provide a good radial fit within the vessel, even when the delivery system is positioned off-centre and/or the vessel is curved.
5. When deployed the cooperating stents open radially to give a stable cylindrical form perpendicular to the vessel walls.
6. "Bird Beaking" does not occur during the deployment of the stent graft prosthesis of the present invention.
7. Use of the stent graft prosthesis of the present invention has an atraumatic effect on the vessel wall of the vessel it is located within due to offering no sharp points at the proximal (leading during delivery) end of the stent graft prosthesis.

8. The above-mentioned atraumatic effect is achievable with shape-set ring stents having shape set hinge portions and curvilinear portions between the hinge portions, where the curvilinear portions provide proximal apexes which project beyond the fabric of the tubular fabric member and have a larger radius than the distal apexes of the hinge portions which hinge portions are fastened only at selected parts within the tubular fabric member (FIGS. 5 & 8). Alternatively in embodiments using saddle ring stents, a steep saddle-shaped ring stent may be positioned within or over a less steep saddle-shaped ring stent or planar ring stent fastened at the end of the tubular fabric member such that curvilinear "peaks" of the steep saddle-shaped ring stent protrude beyond the end of the tubular fabric member (FIGS. 4a, 4b and 4c).

9. Stability of an end ring stent is achievable with only one other ring stent arranged to cross over or intersect the end ring stent to be stabilised.

10. The radial stability which is achievable to maintain the patency of the lumen of the stent graft prosthesis can be achieved by having either one of the two cooperating ring stents of different configurations crossing over the other one of the two cooperating ring stents of different configurations on the inside or outside.

The following paragraphs relate to embodiments and alternative configurations or preferred aspects of the disclosed stent graft prostheses.

(a) A stent graft prosthesis comprising:
a tubular fabric member having at least first and second ends, and a length $L_f$ extending between the first and second ends, and having an open lumen diameter $D_f$; wherein at least one of the first and second ends of the tubular fabric member is supported by a combination of two cooperating ring stents of different configurations, and each one of the two cooperating ring stents of different configurations is compressible into a folded shape to provide a compact delivery form of the stent graft prosthesis, and the tubular fabric member is attached at selected points to each of the two cooperating ring stents of different configurations, and if the tubular fabric member is supported throughout its length by any additional stents, none of any additional stents contact either one of the two cooperating ring stents of different configurations in the combination of two cooperating ring stents of different configurations when the stent graft prosthesis is in a deployed form.

(b). A stent graft prosthesis comprising:
a tubular fabric member having at least first and second ends, and a length $L_f$ extending between the first and second ends, and having an open lumen diameter $D_f$; wherein at least one of the first and second ends of the tubular fabric member is supported by a combination of two cooperating ring stents of different configurations, and each one of the two cooperating ring stents of different configurations is compressible into a folded shape to provide a compact delivery form of the stent graft prosthesis, and the tubular fabric member is attached at selected points to each of the two cooperating ring stents of different configurations, and the two cooperating ring stents of different configurations are free to move relative to one another at points where one of the two cooperating ring stents of different configurations crosses the other one of the two cooperating ring stents of different configurations, and that one of the two cooperating ring stents of different configurations is constrained from over-dilation by the other one of the two cooperating ring stents of different configurations.

(c). A stent graft prosthesis as mentioned in paragraph (a) or paragraph (b), wherein at least one of the two cooperating ring stents of different configurations that is compressible into a folded shape has a diameter that equals or exceeds the open lumen diameter $D_f$ of the tubular fabric member.

(d). A stent graft prosthesis as mentioned in paragraph (c), wherein one of the two cooperating ring stents of different configurations that is compressible into a folded shape has a diameter that exceeds the diameter of the other one of the two cooperating ring stents of different configurations that is compressible into a folded shape.

(e). A stent graft prosthesis as mentioned in any one of paragraphs (a), (b), (c) or (d), wherein one of the two cooperating ring stents of different configurations that is compressible into a folded shape is a shape-set ring stent having at least one "V"-shaped hinge portion.

(f). A stent graft prosthesis as mentioned in any one of paragraphs (a), (b), (c) or (d), wherein one of the two cooperating ring stents of different configurations that is compressible into a folded shape is a shape-set ring stent having more than one "V"-shaped hinge portion, and curvilinear portions therebetween.

(g). A stent graft prosthesis as mentioned in any one of paragraphs (a), (b), (c) or (d), wherein one of the two cooperating ring stents of different configurations that is compressible into a folded shape is a shape-set ring stent having multiple connected "V"-shaped hinge portions, optionally, a Z-stent configuration.

(h). A stent graft prosthesis as mentioned in any one of paragraphs (e), (f) or (g), wherein the shape-set ring stent is compressible radially into a folded shape and expansible radially within the open lumen diameter $D_f$ of the tubular fabric member, and is located on an end of the tubular fabric member such that a portion of the shape-set ring stent extends beyond the length $L_f$ of the tubular fabric member and is not covered by fabric of the tubular fabric member.

(i). A stent graft prosthesis as mentioned in paragraph (h), wherein "V"-shaped hinge portions of the shape-set ring lie within the length $L_f$ of the tubular fabric member.

(j). A stent graft prosthesis as mentioned in any one of paragraphs (e), (f), (g) or (h), wherein the shape-set ring stent having at least one "V"-shaped hinge portion is positioned at least in part within the other one of the two cooperating ring stents of different configurations, which other one of the two cooperating ring stents of different configurations is compressible into a "saddle"-shape having peak and valley portions, and the shape-set ring stent is attached to the fabric of the tubular fabric member by the "V"-shaped hinge portion, or respective "V"-shaped hinge portions of the shape-set ring stent, at a peak of the "saddle"-shaped ring stent (FIG. 5).

(k). A stent graft prosthesis as mentioned in paragraph (j), wherein the tubular fabric member has a substantially circular perimeter at each of the first and second ends, and the ring stent which is compressible into a "saddle"-shape is attached to the fabric of the tubular fabric member at multiple points around the substantially circular perimeter of one of the first and second ends, and the cooperating shape-set ring stent is selectively attached to parts of the fabric of the tubular fabric member at the same end to allow the ring stent which is compressible into a "saddle"-shape having peak and valley portions to slide when necessary on the shape-set ring stent.

(l). A stent graft prosthesis as mentioned in any one of paragraphs (a), (b), (c) (d), (e), (f), (g), (h), (i), (j), or (k), wherein the different configurations of the two cooperating ring stents includes that one of the two cooperating ring stents of different configurations forms a relatively steep "saddle"-shaped ring stent in comparison with the other one of the two cooperating ring stents of different configurations.

(m). A stent graft prosthesis as mentioned in any one of paragraphs (a), (b), (c) or (d), wherein each of the two cooperating ring stents of different configurations that is compressible into a folded shape is compressible into a "saddle"-shape having peak and valley portions, wherein one of the two cooperating ring stents has an uncompressed diameter $d_1$ that is greater than or equal to the open lumen diameter $D_f$ of the tubular fabric member and the other one of the two cooperating ring stents has an uncompressed diameter $d_2$ that is greater than the open lumen diameter $D_f$ of the tubular fabric member and that is significantly greater than the diameter $d_1$, and the one of the two cooperating ring stents which has an uncompressed diameter $d_1$ overlaps the other one of the two cooperating ring stents which has an uncompressed diameter $d_2$ so as to constrain the latter without being attached to it.

(n). A stent graft prosthesis as mentioned in paragraph (m) wherein the one of the two cooperating ring stents which has an uncompressed diameter $d_1$ crosses the other one of the two cooperating ring stents which has an uncompressed diameter $d_2$ at 4 points of intersection, each point of intersection lying in a region between peak and valley portions of the ring stent which has an uncompressed diameter $d_2$.

(o). A stent graft prosthesis as mentioned in paragraph (m), wherein the one of the two cooperating ring stents which has an uncompressed diameter $d_2$ is attached to the fabric of the tubular fabric member such that in the "saddle"-shape configuration, "valley" portions thereof are attached within the tubular fabric member, and "peak" portions protrude beyond the length $L_f$ of the tubular fabric member and are not covered by fabric of the tubular fabric member.

(p). A stent graft prosthesis as mentioned in any one of the preceding paragraphs wherein one of the two cooperating ring stents at each of the first and second ends of the tubular fabric member has curvilinear portions exposed beyond the length $L_f$ of the tubular fabric member, wherein the exposed curvilinear portions are either bare stent, or covered or coated with material to mitigate traumatic contact with a natural vessel wall.

The illustrated embodiments are provided by way of non-limiting examples of stent graft prosthesis devices enabled by the stent combinations developed by the present inventors. Modifications and improvements may be incorporated without departing from the scope of the invention as disclosed herein and claimed hereinafter.

What is claimed is:

1. A stent graft prosthesis comprising:
   a tubular fabric member having at least first and second ends, and a length $L_f$ extending between the first and second ends, and having an open lumen diameter $D_f$;

wherein at least one of the first and second ends of the tubular fabric member is supported by a combination of two cooperating ring stents of different configurations, and each one of the two cooperating ring stents of different configurations is compressible into a folded shape to provide a compact delivery form of the stent graft prosthesis, wherein one of the two cooperating ring stents of different configurations that is compressible into a folded shape is a Z-shaped stent having a V-shaped hinge portion fastened to an inner surface of the tubular fabric member, the Z-shaped stent being located within the other of the two cooperating ring stents of different configurations which is a saddle-shaped stent, the V-shaped hinge portion being attached to the inner surface of the tubular fabric member only in the vicinity of a peak portion of the second ring stent such that independent relative motion is possible with one stent sliding across contact points with the other stent;

and the tubular fabric member is attached at selected points to each of the two cooperating ring stents of different configurations, and wherein one of the two cooperating ring stents at the at least one of the first and second ends of the tubular fabric member has curvilinear portions exposed beyond the length $L_f$ of the tubular fabric member.

2. A stent graft prosthesis according to claim 1, wherein the other one of the two cooperating ring stents of different configurations is also compressible into a folded saddle shape having two peaks and two valleys, and a peak thereof is axially aligned with a peak of the at least one of the two cooperating ring stents of different configurations.

3. A stent graft prosthesis according to claim 1, wherein the other one of the two cooperating ring stents of different configurations that is compressible into a folded shape is a shape-set ring stent having at least one V-shaped hinge portion, and that V-shaped hinge portion is axially aligned with a peak of the at least one of the two cooperating ring stents of different configurations.

4. A stent graft prosthesis as claimed in claim 1, wherein the other one of the two cooperating ring stents of different configurations that is compressible into a folded shape is a shape-set ring stent having more than one V-shaped hinge portion, and curvilinear portions therebetween.

5. A stent graft prosthesis as claimed in claim 1, wherein the exposed curvilinear portions are either bare stent, or covered or coated with material to mitigate traumatic contact with a natural vessel wall.

6. A stent graft prosthesis as claimed in claim 5, wherein the curvilinear portions provide proximal apexes which project beyond the fabric of the tubular fabric member and have a larger radius than the distal apexes of the hinge portions which hinge portions are fastened only at selected parts within the tubular fabric member.

7. A stent graft prosthesis as claimed in claim 5, wherein the curvilinear portions are peaks of a saddle-shaped ring stent which peaks protrude beyond the end of the tubular fabric member.

8. A stent graft prosthesis as claimed in claim 1, wherein at least one of the two cooperating ring stents of different configurations that is compressible into a folded shape has a diameter that equals or exceeds the open lumen diameter $D_f$ of the tubular fabric member.

9. A stent graft prosthesis as claimed in claim 8, wherein one of the two cooperating ring stents of different configurations that is compressible into a folded shape has a diameter that exceeds the diameter of the other one of the two cooperating ring stents of different configurations that is compressible into a folded shape.

10. A stent graft prosthesis as claimed in claim 3, wherein the shape-set ring stent is compressible radially into a folded shape and expansible radially within the open lumen diameter $D_f$ of the tubular fabric member, and is located on an end of the tubular fabric member such that a portion of the shape-set ring stent extends beyond the length $L_f$ of the tubular fabric member and is not covered by fabric of the tubular fabric member.

11. A stent graft prosthesis as claimed in claim 10, wherein V-shaped hinge portions of a shape-set ring lie within the length $L_f$ of the tubular fabric member.

12. A stent graft prosthesis as claimed in claim 1, wherein each of the two cooperating ring stents of different configurations that is compressible into a folded shape is compressible into a saddle-shape having peak and valley portions, wherein one of the two cooperating ring stents has an uncompressed diameter $d_1$ that is greater than or equal to the open lumen diameter $D_f$ of the tubular fabric member and the other one of the two cooperating ring stents has an uncompressed diameter $d_2$ that is greater than the open lumen diameter $D_f$ of the tubular fabric member and that is greater than the diameter $d_1$, and the one of the two cooperating ring stents which has an uncompressed diameter $d_1$ overlaps the other one of the two cooperating ring stents which has an uncompressed diameter $d_2$ so as to constrain the latter without being attached to it.

13. A stent graft prosthesis comprising:
a tubular fabric member having at least first and second ends, and a length $L_f$ extending between the first and second ends, and having an open lumen diameter $D_f$;
wherein at least one of the first and second ends of the tubular fabric member is supported by a combination of two cooperating ring stents of different configurations, one of the two cooperating ring stents of different configurations having at least one V-shaped portion attached to the tubular fabric member at only the at least one V-shaped portion, and each one of the two cooperating ring stents of different configurations is compressible into a folded shape to provide a compact delivery form of the stent graft prosthesis, and the tubular fabric member is attached at selected points to each of the two cooperating ring stents of different configurations, and the two cooperating ring stents of different configurations are free to move relative to one another at points where one of the two cooperating ring stents of different configurations crosses the other one of the two cooperating ring stents of different configurations, and that one of the two cooperating ring stents of different configurations is constrained from over-dilation by the other one of the two cooperating ring stents of different configurations; and
wherein one of the two cooperating ring stents at the at least one of the first and second ends of the tubular fabric member has curvilinear portions exposed beyond the length $L_f$ of the tubular fabric member.

14. A stent graft prosthesis comprising:
a tubular graft member;
a shape-set foldable ring stent having one or more V-shaped hinge portions and curvilinear portions therebetween, wherein the shape-set foldable ring is attached to the tubular graft member along only the V-shaped hinge portions, in combination with an outer ring stent that is compressible into a folded saddle shape having two peaks and two valleys portions, as combined end-sealing stents for the tubular fabric member of a stent graft prosthesis to be deployed as a repair in a natural vessel, the saddle shaped end ring stent having two peak and two valley portions and being configured as the overlying outer ring stent and slidably crossing portions of the shape-set foldable ring stent whereby upon deployment of the stent graft prosthesis the shape-set ring stent expands radially, and perpendicularly to the walls of the natural vessel being repaired which radial expansion urges the saddle shaped ring stent into a desired round cross-sectional shape whilst preventing the outer saddle shaped end ring stent from distorting into a so-called petal-shape or ovalling deformation; and
wherein one of the two cooperating ring stents at the at least one of the first and second ends of the tubular fabric member has curvilinear portions exposed beyond the length $L_f$ of the tubular fabric member.

* * * * *